US011802822B2

(12) United States Patent
Quevedo et al.

(10) Patent No.: US 11,802,822 B2
(45) Date of Patent: Oct. 31, 2023

(54) MULTIPLEXED EXPANSION (MULTIEXM) PATHOLOGY

(71) Applicant: Massachusetts Institute of Technology, Cambridge, MA (US)

(72) Inventors: Pablo Valdes Quevedo, Boston, MA (US); Yongxin Zhao, Quincy, MA (US); Edward Stuart Boyden, Chestnut Hill, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 471 days.

(21) Appl. No.: 17/111,135

(22) Filed: Dec. 3, 2020

(65) Prior Publication Data

US 2021/0190652 A1 Jun. 24, 2021

Related U.S. Application Data

(60) Provisional application No. 62/944,195, filed on Dec. 5, 2019.

(51) Int. Cl.
| | | |
|---|---|---|
| *G01N 1/36* | (2006.01) | |
| *C08L 101/14* | (2006.01) | |
| *G01N 1/30* | (2006.01) | |

(52) U.S. Cl.
CPC .............. *G01N 1/36* (2013.01); *C08L 101/14* (2013.01); *G01N 2001/305* (2013.01); *G01N 2001/364* (2013.01)

(58) Field of Classification Search
None
See application file for complete search history.

(56) References Cited

U.S. PATENT DOCUMENTS

| 5,952,232 A | 9/1999 | Rothman |
| 6,107,081 A | 8/2000 | Feeback et al. |
| 6,204,064 B1 | 3/2001 | Alberts et al. |
| 6,271,278 B1 | 8/2001 | Park et al. |
| 6,287,870 B1 | 9/2001 | Wardlaw et al. |
| 10,059,990 B2 | 8/2018 | Boyden et al. |
| 10,309,879 B2 | 6/2019 | Chen et al. |
| 10,317,321 B2 | 6/2019 | Tillberg et al. |
| 10,364,457 B2 | 7/2019 | Wassie et al. |
| 10,526,649 B2 | 1/2020 | Chen et al. |
| 10,563,257 B2 | 2/2020 | Boyden et al. |
| 10,774,367 B2 | 9/2020 | Fraser et al. |
| 10,995,361 B2 | 5/2021 | Chen et al. |
| 11,180,804 B2 | 11/2021 | Chen et al. |
| 11,408,890 B2 | 8/2022 | Boyden et al. |
| 2002/0176880 A1 | 11/2002 | Cruise et al. |
| 2003/0120231 A1 | 6/2003 | Wang et al. |
| 2004/0115629 A1 | 6/2004 | Panzer et al. |
| 2004/0137527 A1 | 7/2004 | Sleytr et al. |
| 2004/0248326 A1 | 12/2004 | Ziaie et al. |
| 2005/0034990 A1 | 2/2005 | Crooks et al. |
| 2005/0069877 A1 | 3/2005 | Gandhi et al. |
| 2005/0090016 A1 | 4/2005 | Rich et al. |
| 2005/0169962 A1 | 8/2005 | Bhatia et al. |
| 2005/0196702 A1 | 9/2005 | Bryant et al. |
| 2006/0000767 A1 | 1/2006 | Trauger et al. |
| 2006/0003356 A1 | 1/2006 | Shaw et al. |
| 2006/0110760 A1 | 5/2006 | Kim et al. |
| 2006/0115146 A1 | 6/2006 | Ogura et al. |
| 2006/0165912 A1 | 7/2006 | Koberstein et al. |
| 2007/0023942 A1 | 2/2007 | Andino et al. |
| 2007/0042954 A1 | 2/2007 | Chen et al. |
| 2007/0134902 A1 | 6/2007 | Bertino et al. |
| 2007/0177786 A1 | 8/2007 | Bartels |
| 2008/0139407 A1 | 6/2008 | Slootstra et al. |
| 2008/0261834 A1 | 10/2008 | Simon et al. |
| 2008/0286360 A1 | 11/2008 | Shoichet et al. |
| 2009/0011141 A1 | 1/2009 | Carter et al. |
| 2009/0011420 A1 | 1/2009 | Barron et al. |
| 2009/0096133 A1 | 4/2009 | Doyle et al. |
| 2009/0191627 A1 | 7/2009 | Fadeev et al. |
| 2009/0241681 A1 | 10/2009 | Machauf et al. |
| 2010/0041128 A1 | 2/2010 | Banes et al. |
| 2010/0055161 A1 | 3/2010 | Ahn |
| 2010/0056445 A1 | 3/2010 | Sharma et al. |
| 2010/0068725 A1 | 3/2010 | Armbruster et al. |
| 2010/0096334 A1 | 4/2010 | Edmiston et al. |

(Continued)

FOREIGN PATENT DOCUMENTS

| CN | 104350372 A | 2/2015 |
| EP | 3159361 A1 | 4/2017 |

(Continued)

OTHER PUBLICATIONS

Cho et al. "Expansion microscopy" (2018), Journal of Microscopy, vol. 271, issue 2: 123-128. (Year: 2018).*
Caprette, "Experimental Biosciences: Resources for introductory & intermediate level laboratory courses" (2012), available on-line at https://www.ruf.rice.edu/~bioslabs/studies/sds-page/denature.html (Year: 2012).*
Duan, C. et al., "Application of antigen retrieval method in hMAM immunohistochemical staining of old paraffin-embedded specimens", Academy of Military Medical Sciences, vol. 38(12), Dec. 31, 2014, 965-967.
Ferri, A., "Expansion Microscopy: A New Approach to Microscopic Evaluation", Master's thesis, retrieved from https://scholarcommons.sc.edu/etd/6034, 2020.

(Continued)

*Primary Examiner* — Teresa E Knight
(74) *Attorney, Agent, or Firm* — Pierce Atwood LLP

(57) ABSTRACT

The invention provides a method for preparing an expanded biological specimen suitable for microscopic analysis. Expanding the biological sample can be achieved by anchoring biomolecules to a polymer network and swelling, or expanding, the polymer network, thereby moving the biomolecules apart as further described below. As the biomolecules are anchored to the polymer network isotropic expansion of the polymer network retains the spatial orientation of the biomolecules resulting in an expanded, or enlarged, biological specimen.

23 Claims, 17 Drawing Sheets

(56) References Cited

U.S. PATENT DOCUMENTS

| | | |
|---|---|---|
| 2010/0111396 A1 | 5/2010 | Boucheron |
| 2010/0119755 A1 | 5/2010 | Chung et al. |
| 2010/0248977 A1 | 9/2010 | Johnston et al. |
| 2011/0009171 A1 | 1/2011 | Watanabe et al. |
| 2011/0070604 A1 | 3/2011 | Gimzewski et al. |
| 2011/0087315 A1 | 4/2011 | Richardson-Burns et al. |
| 2011/0091717 A1 | 4/2011 | Weiss et al. |
| 2011/0091922 A1 | 4/2011 | Krishnan et al. |
| 2011/0291357 A1 | 12/2011 | Boyle |
| 2012/0025271 A1 | 2/2012 | Nakano |
| 2012/0184670 A1 | 7/2012 | Kobayashi et al. |
| 2012/0220478 A1 | 8/2012 | Shaffer |
| 2012/0251527 A1 | 10/2012 | Reiser |
| 2012/0310223 A1 | 12/2012 | Knox et al. |
| 2013/0045503 A1 | 2/2013 | Miyawaki et al. |
| 2013/0203605 A1 | 8/2013 | Shendure et al. |
| 2014/0087139 A1 | 3/2014 | Rowley et al. |
| 2014/0193651 A1 | 7/2014 | Kharlampieva et al. |
| 2014/0364330 A1 | 12/2014 | Mershin et al. |
| 2015/0087001 A1 | 3/2015 | Gradinaru et al. |
| 2015/0226743 A1 | 8/2015 | Weiss et al. |
| 2015/0353989 A1 | 12/2015 | Fraser et al. |
| 2015/0370961 A1 | 12/2015 | Zhang et al. |
| 2015/0376261 A1 | 12/2015 | Steyaert et al. |
| 2016/0116384 A1 | 4/2016 | Boyden et al. |
| 2016/0252528 A1 | 9/2016 | Sangaralingham et al. |
| 2016/0265046 A1 | 9/2016 | Zhang et al. |
| 2016/0304952 A1 | 10/2016 | Boyden et al. |
| 2016/0305856 A1 | 10/2016 | Chen et al. |
| 2017/0067096 A1 | 3/2017 | Wassie et al. |
| 2017/0081489 A1 | 3/2017 | Boyden et al. |
| 2017/0087489 A1 | 3/2017 | Terlingen et al. |
| 2017/0089811 A1 | 3/2017 | Chen et al. |
| 2017/0103521 A1 | 4/2017 | Chukka et al. |
| 2017/0182220 A1 | 6/2017 | Song et al. |
| 2017/0199104 A1 | 7/2017 | Gradinaru et al. |
| 2017/0276598 A1 | 9/2017 | Ikuyama |
| 2017/0323431 A1 | 11/2017 | Sarkar et al. |
| 2018/0119219 A1 | 5/2018 | Chen et al. |
| 2019/0064037 A1 | 2/2019 | Boyden et al. |
| 2019/0071656 A1 | 3/2019 | Chang et al. |
| 2019/0113423 A1 | 4/2019 | Goodman et al. |
| 2019/0256633 A1 | 8/2019 | Gao et al. |
| 2020/0041514 A1 | 2/2020 | Boyden et al. |
| 2020/0049599 A1 | 2/2020 | Alexander et al. |
| 2020/0081005 A1 | 3/2020 | Boyden et al. |
| 2020/0217853 A1 | 7/2020 | Estandian et al. |
| 2020/0271556 A1 | 8/2020 | Sarkar et al. |
| 2021/0130882 A1 | 5/2021 | Boyden et al. |
| 2021/0196856 A1 | 7/2021 | Boyden et al. |

FOREIGN PATENT DOCUMENTS

| | | |
|---|---|---|
| JP | 2005291759 A | 10/2005 |
| JP | 2006036957 A | 2/2006 |
| JP | 2008286694 A | 11/2008 |
| JP | 2009191125 A | 8/2009 |
| JP | 2014005231 A | 1/2014 |
| WO | 0008212 A1 | 2/2000 |
| WO | 2007103665 A2 | 9/2007 |
| WO | 2008058302 A1 | 5/2008 |
| WO | 2010048605 A1 | 4/2010 |
| WO | 2012142664 A1 | 10/2012 |
| WO | 2014025392 A1 | 2/2014 |
| WO | 2014152984 A1 | 9/2014 |
| WO | 2015041755 A1 | 3/2015 |
| WO | 2015127183 A2 | 8/2015 |
| WO | 2016040489 A1 | 3/2016 |
| WO | 2017027367 A1 | 2/2017 |
| WO | 2017027368 A1 | 2/2017 |
| WO | 2017031249 | 2/2017 |
| WO | 2017079406 A1 | 5/2017 |
| WO | 2017147435 A1 | 8/2017 |
| WO | 2018157074 A1 | 8/2018 |
| WO | 2019144391 A1 | 8/2019 |
| WO | 2021051011 A1 | 3/2021 |

OTHER PUBLICATIONS

New England BioLabs, "Proteinase K", P8102S product datasheet, 1 page, accessed Nov. 17, 2020.
Office Action dated Apr. 4, 2018 from U.S. Appl. No. 14/627,310, filed Feb. 20, 2015.
Product information brochure, FLOCRYL™ MBA, SNF Floerger, pp. 1-4, accessed Nov. 17, 2020.
"Crosslinking and Photoactivatable Reagents", Invitrogen, Chapter 5 in "Molecular Probes™ Handbook a Guide to Fluorescent Probes and Labeling Technologies", 11th Edition, 2010, 171-188.
"Epitope Recovery Methods for IHC", Nov. 7, 2015, ThermoFisher Scientific, pp. 1-2.
"Proteinase K from Tritirachium album, solution", Serva Electrophoresis, Instruction Manual, Cat. No. 33755, 1 page, publicly available prior to Feb. 1, 2017.
Al, H. et al., "Exploration of new chromophore structures leads to the identification of improved blue fluorescent proteins", Biochemistry, 46, 2007, 5904-10.
Akhavan, A. et al., "Molecular Epizootiology of Rodent Leishmaniasis in a Hyperendemic Area of Iran", Iranian J Publ Health, vol. 39, No. 1, 2010, 1-7.
Asano, S. M. et al., "Expansion Microscopy: Protocols for Imaging Proteins and RNA in Cells and Tissues", Current Protocols in Cell Bio., vol. 80, No. 1, Online: DOI: 10.1002/cpcb.56. Retrieved from the Internet: URL:https://onlinelibrary.wiley.com/doi/full-xml/10.1002/cpcb.56> [retrieved on Feb. 26, 2021], Sep. 2, 2018, pp. 41.
Bates, M. et al., "Multicolor super-resolution imaging with photoswitchable fluorescent probes", Science, 317, 2007, 1749-1753.
Batish, M. et al., "Neuronal mRNAs Travel Singly into Dendrites", PNAS, vol. 109(12), 2012, 4645-4650.
Beliveau, B. et al., "Versatile design and synthesis platform for visualizing genomes with Oligopaint FISH probes", PNAS, vol. 109(52): pfa, 2012, 21301-21306.
Bi, X. et al., "In situ-forming cross-linking hydrogel systems: chemistry and biomedical applications", In: "Emerging Concepts in Analysis and Applications of Hydrogels", INTECH, Aug. 24, 2016, 131-158.
Bleckmann, J. et al., "Surface-Layer Lattices as Patterning Element for Multimeric Extremozymes", Small Journal, 2013, 1-8.
Bokman, S. H. et al., "Renaturation of Aequorea gree-fluorescent protein", Biochem. Biophys. Res. Commun., 101, 1981, 1372-80.
Bossi, M. et al., "Multicolor far-field fluorescence nanoscopy through isolated detection of distinct molecular species", Nano Lett., 8, 2008, 2463-8.
Breitwieser, A. et al., "Magnetic Beads Functionalized with Recombinant S-Layer Protein Exhibit High Human IgG-Binding and Anti-Fouling Properties", Current Topics in Peptide & Protein Research, vol. 17, 2016, 45-55.
Bruchez, M. et al., "Semiconductor nanocrystals as fluorescent biological labels", Science, vol. 281, 1998, 2013-6.
Buckley, P. et al., "Cytoplasmic Intron Sequence-Retaining Transcripts Can Be Dendritically Targeted via ID Element Retrotransposons", Neuron, vol. 69, 2011, 877-884.
Buenrostro, J. D. et al., "ATAC-seq: A Method for Assaying Chromatin Accessibility Genome-Wide: ATAC-seq for Assaying Chromatin Accessibility", In: "Current Protocols in Molecular Biology", Wiley, New York, NY, Jan. 5, 2015.
Buxbaum, A. et al., "Single-Actin mRNA Detection in Neurons Reveals a Mechanism for Regulating Its Translatability", Science, vol. 343, 2014, 419-422.
Cabili, M. et al., "Localization and abundance analysis of human lncRNAs at single-cell and single-molecule resolution", Genome Biology, vol. 16(20), 2015, 1-16.
Cai, et al., Nat Meth., 10, 2013, 540-547.
Cajigas, I. et al., "The local transcriptome in the synaptic neuropil revealed by deep sequencing and high-resolution imaging", Neuron 74, 2012, 453-466.

(56) References Cited

OTHER PUBLICATIONS

Cao, W., "DNA ligases and ligase-based technologies", Clinical and Applied Immunology Reviews, Elsevier, Amsterdam, NL, vol. 2, No. 1, Jan. 15, 2001, 33-43.
Carpenter, A. E. et al., "CellProfiler: image analysis software for identifying and quantifying cell phenotypes", Genome Biol., 7, 2006, R100.
Chang, J-B et al., "Iterative expansion microscopy", Nature Methods, 14(6), Jun. 2017, 593-599.
Chen, F. et al., "Expansion Microscopy", Science, 347(6621):, Jan. 15, 2015, 1-18.
Chen, F. et al., "Nanoscale Imaging of RNA with Expansion Microscopy", Nature Methods, 13(8), Aug. 2016, 679-684.
Chen, F. et al., "Supplementary Material for Expansion Microscopy", Science, 347(6221), Jan. 15, 2015, 543-548.
Chen, K. et al., "Spatially resolved, highly multiplexed RNA profiling in single cells", Science. vol. 348(6233), 2015, aaa6090-aaa6090.
Chen, X. et al., "[Supplementary material] ATAC-see reveals the accessible genome by transposase-mediated imaging and sequencing", Nature Methods, vol. 13, No. 12, Oct. 17, 2016, 1813-1828.
Choi, H. et al., "Next-Generation in Situ Hybridization Chain Reaction: Higher Gain, Lower Cost, Greater Durability", ACS Nano 8(5), 2014, 4284-4294.
Choi, H. et al., "Programmable in situ amplification for multiplexed imaging of mRNA expression", Nature Biotechnology, 28(11), 2010, 1208-1212.
Chozinski, T. et al., "Expansion microscopy with conventional antibodies and fluorescent proteins", Nature Methods, vol. 13(6), 2016, 485-491.
Chu, J. et al., "Non-invasive intravital imaging of cellular differentiation with a bright red-excitable fluorescent protein", Nat. Methods, 11, 2014, 572-8.
Clemson, C. et al., "An architectural role for a nuclear noncoding RNA: NEAT1 RNA is essential for the structure of paraspeckles", Molecular Cell, 33, 2009, 717-26.
Cormack, B. P. et al., "FACS-optimized mutants of the green fluorescent protein (GFP)", Gene, 173, 1996, 33-8.
Cubitt, A. B. et al., "Understanding structure-function relationships in the Aequorea victoria green fluorescent protein", Methods Cell Biol., 58, 1999, 19-30.
Dedecker, P. et al., "Localizer: fast, accurate, open-source, and modular software package for superresolution microscopy", J. Biomed. Opt., 17, 2012, 126008.
Dilorenzo, F. et al., "Nanostructural Heterogeneity in Polymer Networks and Gels", Polymer Chemistry, vol. 6, 2015, 5515-5528.
Edelstein, A. et al., "Computer control of microscopes using μManager", Curr. Protoc. Mol. Biol. Chapter 14, Unit14.20, 2010.
English, B. P. et al., "A three-camera imaging microscope for high-speed single-molecule tracking and super-resolution imaging in living cells", Proc SPIE Int Soc for Opt Eng., 9550, Aug. 21, 2015, 1-11.
Engreitz, J. et al., "The Xist lncRNA exploits three-dimensional genome architecture to spread across the X chromosome", Science 341, 2013, 1237973.
Femino, A. et al., "Visualization of Single RNA Transcripts in Situ", Science, vol. 280, 1998, 585-590.
Feng, G. et al., "Imaging neuronal subsets in transgenic mice expressing multiple spectral variants of GFP", Neuron, 28, 2000, 41-51.
Filonov, G. S. et al., "Bright and stable near-infrared fluorescent protein for in vivo imaging", Nat. Biotechnol., 29, 2011, 757-61.
Fouz, M. et al., "Bright Fluorescent Nanotags from Bottlebrush Polymers with DNA-Tipped Bristles", ACS Central Science, vol. 1, 2015, 431-438.
Freifeld, L. et al., "Expansion microscopy of zebrafish for neuroscience and developmental biology studies", PNAS (online), Nov. 21, 2017, E10799-E10808.

Goedhardt, J. et al., "Structure-guided evolution of cyan fluorescent proteins towards a quantum yield of 93%", Nat. Commun., 3, 2012, 751.
Goor, Olga J. et al., "Introduction of anti-fouling coutings at the surface of supramolecular elastomeric materials via post-modification of reactive supramolecular additives", Polymer Chem., vol. 8, No. 34, Jan. 1, 2017, 5228-5238.
Griesbeck, O. et al., "Reducing the environmental sensitivity of yellow fluorescent protein. Mechanism and applications", J. Biol. Chem., 276, 2001, 29188-94.
Gurskaya, N. G. et al., "Engineering of a monomeric green-to-red photoactivatable fluorescent protein induced by blue light", Nat. Biotechnol., 24, 2006, 461-5.
Gyorvary, E. S. et al., "Self-Assembly and Recrystallization of Bacterial S-Layer Proteins at Silicon Supports Imaged in Real Time by Atomic Force Microscopy", Journal of Microscopy, vol. 212, 2003, 300-306.
Habuchi, S. et al., "mKikGR, a monomeric photoswitchable fluorescent protein", PLoS One, 3, 2008, e3944.
Hackstadt, T., "Steric hindrance of antibody binding to surface proteins of Coxiella burnetti by phase I lipopolysaccharide", Infect Immun, 56, 1998, 802-807.
Heim, R. et al., "Engineering green fluorescent protein for improved brightness, longer wavelengths and fluorescence resonance energy transfer", Curr. Biol., 6, 1996, 178-82.
Heim, R. et al., "Wavelength mutations and posttranslational autoxidation of green fluorescent protein", Proc. Natl. Acad. Sci. U.S.A., 91, 1994, 12501-4.
Hoffman, T. L. et al., "A Biosensor Assay for Studying Ligand-Membrane Receptor Interactions: Binding of Antibodies and HIV-1 Env to Chemokine Receptors", PNAS, 97(21), 2000, 11215-11220.
Huang, B. et al., "Whole-cell 3D Storm reveals interactions between cellular structures with nanometer-scale resolution", Nat. Methods, 5, 2008, 1047-1052.
Huisken, J. et al., "Optical Sectioning Deep Inside Live Embryos by Selective Plane Illumination Microscopy", Science. Vol. 305, 2004, 1007-1009.
Hunt, et al., "High temperature antigen retrieval and loss of nuclear morphology: a comparison of microwave\rand autoclave techniques", J. Clin. Pathol. 49, 1996, 767-770.
Jekel, P A. et al., "Use of endoproteinase Lys-C from Lysobacter enzymogenes in protein sequence analysis", Anal. Biochem., 134, 1983, 347-354.
Jiang, Y. et al., "Click hydrogels, microgels and nanogels: emerging platforms for drug delivery and tissue engineering", Biomaterials, vol. 35, No. 18, Jun. 1, 2014, 4969-4985.
Jimenez, N. et al., "A Novel Approach for Intracellular 3D Immuno-Labeling for Electron Tomography", Traffic, 13, 2012, 926-933.
Jung, H. et al., "Axonal mRNA localization and local protein synthesis in nervous system assembly, maintenance and repair", Nat. Rev. Neurosci., vol. 13(5), 2012, 308-24.
Kakimoto, K. et al., "Hypothesis for the mechanism for heat-induced antigen retrieval occurring on fresh frozen sections without formalin-fixation in immunohistochemistry", J Mol Histol., 39, 2008, 389-399.
Kaur, et al., Biochemistry 45, 2006, 7347-7355.
Ke, R. et al., "In situ sequencing for RNA analysis in preserved tissue and cells", Nature Methods, vol. 10(9), 2013, 857-60.
Ke, R. et al., "Supplementary Material In situ sequencing for RNA analysis in preserved tissue and cells", Nature Methods 10(9):857-60, 2013, 1-29.
Kroon, D.-J , "B-spline Grid, Image and Point based Registration", Matlab Cent. at <http://www.mathworks.com/matlabcentral/fileexchange/20057-b-spline-grid--image-and-point-based-registration>, Mar. 16, 2011.
Laemmli, U. K., "Cleavage of structural proteins during the assembly of the head of bacteriophage T4", Nature, 227, 1970, 680-685.
Lam, A. J. et al., "Improving FRET dynamic range with bright green and red fluorescent proteins", Nat. Methods, 9, 2012, 1005-12.
Lee, J. et al., "Highly Multiplexed Subcellular RNA Sequencing in Situ", Duplicate—RefID 308986 Science, vol. 343, 2014, 1360-1363.

(56) References Cited

OTHER PUBLICATIONS

Lee, J. H. et al., "Highly Multiplexed Subcellular RNA Sequencing in Situ", Sciencexpress, online http://www.sciencemag.org/content/early/recent, 6 pages (Science, vol. 343), Feb. 27, 2014.
Lein, E. et al., "Genome-wide atlas of gene expression in the adult mouse brain", Nature, vol. 445, 2007, 168-76.
Levsky, J. et al., "Fluorescence in situ hybridization: past, present and future", Journal of Cell Science, 116, 2003, 2833-2838.
Lieberman-Aiden, E. et al., "Comprehensive mapping of long-range interactions reveals folding principles of the human genome", Science 326, 2009, 289-93.
Livet, J. et al., "Transgenic strategies for combinatorial expression of fluorescent proteins in the nervous system", Nature, 450, 2007, 56-62.
Lowe, D. G., "Distinctive Image Features from Scale-Invariant Keypoints", Int. J. Comput. Vis., 60, 2004, 91-110.
Lubeck, E. et al., "Single-cell in situ RNA profiling by sequential hybridization", Nature Methods, vol. 11(4), 2014, 360-1.
Lubeck, E. et al., "Single-cell systems biology by super-resolution imaging and combinatorial labeling", Nature Methods, vol. 9, 2012, 743-8.
Majcher, M. J. et al., "Hydrogel synthesis and design", In: "Cellulose-Based Superabsorbent Hydrogels", Springer International Publishing, Jan. 1, 2018, 1-41.
Markwardt, M. L. et al., "An improved cerulean fluorescent protein with enhanced brightness and reduced reversible photoswitching", PLoS One, 6, 2011, e17896.
McKinney, S. A. et al., "A bright and photostable photoconvertible fluorescent protein", Nat. Methods, 6, 2009, 131-3.
Meng, H., "Localization of a Blood Pressure Quantitative Trait Locus (QTL) to a 1.7cM Interval on Rat Chromosome 9", Medical College of Ohio, dissertation, 2002, 1-158.
Mito, M. et al., "Simultaneous multicolor detection of RNA and proteins using super-resolution microscopy", Methods, 2015, 1-8.
Mortensen, K. I. et al., "Optimized localization analysis for singlemolecule tracking and super-resolution microscopy", Nat. Methods, 7, 2010, 377-81.
Nagai, T. et al., "A variant of yellow fluorescent protein with fast and efficient maturation for cell-biological applications", Nat. Biotechnol., 20, 2002, 87-90.
Nagre, R. D. et al., "Thermosaline Resistant Acrylamide-Based Polyelectrolyte as Filtration Control Additive in Aqueous-Based Mud", Petroleum and Coal, vol. 56, No. 3, 2014, 222-230.
Nilsson, M. et al., "RNA-templated DNA ligation for transcript ananlysis", Nucleic Acids Research, Information Retrieval Ltd., vol. 29, No. 2, Jan. 15, 2001, 578-581.
Orakdogen, N. et al., "Correlation Between Crosslinking Efficiency and Spatial Inhomogeneity in Poly(acrylamide) Hydrogels", Polymer Bulletin, vol. 57, 2006, 631-641.
Ormo, M. et al., "Crystal structure of the Aequorea victoria green fluorescent protein", Science, 273, 1996, 1392-5.
Oshima, K. et al., "Model Polyelectrolyte Gels Synthesized by End-Linking of Tetra-Arm Polymers with Click Chemistry: Synthesis and Mechanical Properties", Macromolecules, vol. 47, 2014, 7573-7580.
Panning, B. et al., "X chromosome Inactivation is Mediated by by Xist RNA stabilization", Cell. Vol. 90, 1997, 907-16.
Parang, B. et al., "Myeloid translocation genes differentially regulate colorectal cancer programs", Oncogene, vol. 35, 2016, 6341-6349.
Park, Y. N. et al., "Detection of Hepatitis C Virus RNA Using Ligation-Dependent Polymerase Chain Reaction in Formalin-Fixed, Paraffin-Embedded Liver Tissues", Amer. J. of Pathol., vol. 149, No. 5, Nov. 1, 1996, 1485-1491.
Plath, K. et al., "Xist RNA and the mechanism of X chromosome inactivation", Annu. Rev. Genet. 36, 2002, 233-78.
Pum, D. et al., "Reassembly of S-Layer Proteins", Nanotechnology, 2014, 1-15.

Raj, A. et al., "Detection of individual endogenous RNA transcripts in situ using multiple singly labeled probes", Methods in Enzymology, vol. 472 (Elsevier Inc.), 2010, 365-386.
Raj, A. et al., "Imaging individual mRNA molecules using multiple singly labeled probes", Nat. Methods 5(10), 2008, 877-879.
Randall, K. J. et al., "A dual-label technique for the immunohistochemical demonstration of T-lymphocyte subsets in formalin-fixed, paraffin-embedded rat lymphoid tissue", Toxicol. Pathol., 36, 2008, 795-804.
Rego, E. H. et al., "Nonlinear structured-illumination microscopy with a photoswitchable protein reveals cellular structures at 50-nm resolution", Proc. Natl. Acad. Sci. U.S.A., 109, 2012, E135-43.
Reinhart-King, C. A. et al., "Dynamics and Mechanics of EndothelialCell Spreading", Biophysical J, 89(1):, Jul. 1, 2005, 676-689.
Rose, R. et al., "Ocular ascorbate transport and metabolism", A. Comp. Physiol.,100, 1991, 273-85.
Rothbauer, M. et al., "Exploitation of S-Layer Anisotropy: pH-Dependent Nanolayer Orientation for Cellular Micropatterning,", Acs NANO, published online, 2013.
Sakai, T. et al., "Design and Fabrication of a High-Strength Hydrogel with Ideally Homogenous Network Structure from Tetrahedron-Like Macromonomers", Macromolecules, vol. 41, 2008, 5379-5384.
Schindelin, J. et al., "Fiji: an open-source platform for biological-image analysis", Nature Methods, vol. 9, 2012, 676-82.
Schnell, U. et al., "Immunolabeling artifacts and the need for live-cell imaging", Nat. Methods, 9, 2012, 152-158.
Seneviratne, U. et al., "S-nitrosation of proteins relevant to Alzheimer's disease during early stages of neurodegeneration", PNAS, vol. 113, No. 15, Apr. 12, 2016, 4152-4157.
Shah, S. et al., "Single-molecule RNA detection at depth via hybridization chain reaction and tissue hydrogel embedding and clearing", Development in Review, 2016.
Shaner, N. C. et al., "Improved monomeric red, orange and yellow fluorescent proteins derived from *Discosoma* sp. red fluorescent protein", Nat. Biotechnol., 22, 2004, 1567-72.
Shaner, N. C. et al., "Improving the photostability of bright monomeric orange and red fluorescent proteins", Nat. Methods, 5, 2008, 545-51.
Shcherbakova, D. M., "An orange fluorescent protein with a large Stokes shift for single-excitation multicolor FCCS and FRET imaging", J. Am. Chem. Soc., 134, 2012, 7913-23.
Shcherbo, D. et al., "Far-red fluorescent tags for protein imaging in living tissues", Biochem. J., 418, 2009, 567-74.
Sleytr, U. et al., "Heterologous Reattachment of Regular Arrays of Glycoproteins on Bacterial Surfaces", Nature, vol. 257, 1975, 400-401.
Sleytr, U. et al., "S-Layers Principles and Applications", FEMS Microbiology Rev., 2014, 1-42.
Sniegowski, J. A. et al., "Maturation efficiency, trypsin sensitivity, and optical properties of Arg96, Glu222, and Gly67 variants of green fluorescent protein", Biochem. Biophys. Res. Commun., 332, 2005, 657-63.
Steward, O. et al., "Compartmentalized synthesis and degradation of proteins in neurons", Neuron, vol. 40, 2003, 347-359.
Steward, O. et al., "Synaptic activation causes the mRNA for the leg Arc to localize selectively near activated postsynaptic sites on dendrites", Neuron, vol. 21, 1998, 741-751.
Strack, R., "Imaging Bigger is Better for Super-Resolution", Nature Methods, 12(13), Mar. 1, 2015, 169.
Subach, F. V. et al., "Bright monomeric photoactivatable red fluorescent protein for two-color super-resolution sptPALM of live cells", J. Am. Chem. Soc., 132, 2010, 6481-91.
Subach, O. M. et al., "An Enhanced Monomeric Blue Fluorescent Protein with the High Chemical Stability of the Chromophore", PLoS One, 6, 2011, e28674.
Thevenaz, P. et al., "A pyramid approach to subpixel registration based on intensity", IEEE Trans. Image Process., 7, 1998, 27-41.
Tillberg, P. et al., "Protein-Retention Expansion Microscopy of Cells and Tissues Labeled Using Standard Fluorescent Proteins and Antibodies", Nature Biotechnology vol. 34(9), Sep. 9, 2016, 987-995.

(56) References Cited

OTHER PUBLICATIONS

Van Vliet, et al., "The Biomechanics Toolbox: Experimental Approaches for Living Cells and Biomolecules", Acta Materialia, 51, Aug. 23, 2003, 5881-5905.
Vedaldi, A. et al., Vlfeat. in Proc. Int. Conf. Multimed.—MM '10 1469 (ACM Press, 2010).doi:10.1145/1873951.1874249.
Wachter, R. M. et al., "Sensitivity of the yellow variant of green fluorescent protein to halides and nitrate", Curr. Biol., 9, 1999, R628-R629.
Wang, F. et al., "RNAscope: A novel in situ RNA analysis platform for formalin-fixed, paraffin-embedded tissues", Journal of Molecular Diagnostics, vol. 14(1), 2012, 22-29.
Wu, C. C. et al., "A method for the comprehensive proteomic analysis of membrane proteins", Nat. Biotechnol., 21, 2003, 532-8.
Xingqi, C. et al., "ATAC-see reveals the accessible genome by transposase-mediated HJ, imaging and sequencing", Nature Methods, vol. 13, No. 12, Dec. 1, 2016, 1013-1020.
Xu, J. et al., "Bioorthogonally cross-linked hydrogel network with precisely controlled disintegration time over a broad ragne", J. Am. Chem.Soc., vol. 136, No. 11, Mar. 19, 2014, 4105-4108.
Yazici, I. et al., "Spatial Inhomogeneity in Poly(acrylic acid) Hydrogels", Polymer, vol. 46, 2005, 2595-2602.
Yu, C-C et al., "Expansion microscopy of C. elegans", ELIFE, [Online] DOI: 10.7554/eLife.46249. Retrieved from the Internet: URL:https://elifesciences.org/articles/46249> [retrieved on Feb. 26, 2021], May 1, 2020, pp. 125.
Zhang, D. et al., "Dynamic DNA nanotechnology using strand-displacement reactions", Nature Chemistry, vol. 3, 2011, 103-113.
Zhang, R. et al., "Tools for GPCR Drug Discovery", Acta Pharmacologica Sinica, 33, 2012, 372-384.
Zhou, C. et al., "Synthesis and characterization of well-defined PAA-PEG multi-responsive hydrogels by ATRP and click chemistry", RSC ADV., vol. 4, No. 97, Jan. 1, 2014, 54631-54640.
Zimmerman, T. A. et al., "Adapting the stretched sample method from tissue profiling to imaging", Proteomics, 8, 2008, 3809-3815.
Boutin, J. A. "Myristoylation." Cell. Signal, 9(1):15-35. (Jan. 1997) doi: 10.1016/S0898-6568(98)00100-3.
Bullock, G. R. "The current status of fixation for electron microscopy: A review." J. Microsc., 133: 1-15. (1984). doi: 10.1111/j.1365-2818.1984.1000458.x.
Cochilla, A. J. et al. "Monitoring secretory membrane with FM1-43 flourescence." Annu. Rev. Neurosci. 22:1-10 (1999). doi:10.1146/annurev.neuro.22.1.1.
Danilczyk, U. G., et al. "Functional relationship between calreticulin, calnexin, and the endoplasmic reticulum luminal domain of calnexin." J. Biol. Chem. 275(17): 13089-13097 (2000). doi:10.1074/jbc.275.17.13069.
English, A. R. et al. "Endoplasmic reticulum structure and interconnections with other organelles." Cold Spring Harbor Perspectives in Biology 2013;5:a013227. doi :10.1101/cshperspect.a013227.
Guo A. et al. "The Critical Role of Surface Chemistry in Protein Microarrays" in Functional Protein Microarrays in Drug Discovery, edt. Paul Predki, p. 53-71 (CRC press, Boca Raton, 2007).
Guo, H. et al. "An efficient procedure for protein extraction from formalin-fixed, Paraffin-embedded tissues for reverse phase protein arrays." Proteome Sci. 10:56 (2012). doi:10.1188/1477-5958-10-56.
Honig, M. G. et al. "Dil and DiO: versatile fluorescent dyes for neuronal labeling and pathway tracing." Trends Neurosci. 12(9):333-341 (1989). doi:10.1016/0166-2236(89)90040-4.
Honig, M. G. et al. "Fluorescent carbocyanine dyes allow living neurons of identified origin to be studied in long-term cultures." J. Cell Biol. 103:171-187 (1986). doi:10.1083/jcb.103.1.171.
International Search Report and Written Opinion from the International Searching Authority dated Mar. 10, 2021 from corresponding Interational Patent Application No. PCT/US2020/063098 Filed on Dec. 3, 2020.
Jamor, M. C. et al. "Permeabilization of Cell Membranes." in Immunocytochemical Methods and Protocols 588:63-6 (2010). doi: 10.1007/978-1-59745-324-0_9.

Ku, T. et al. "Multiplexed and scalable super-resolution imaging of three-dimensional protein localization in size-adjustable tissues." Nat. Biotechnol. 34(9): 973-981 (2016). doi:10.1038/nbt.3641.
Lakkaraju, A. K. K. et al. "Palmitoylated calnexin is a key component of the ribosome-translocon complex." EMBO J. 31, 1823-1835 (2012). doi:10.1038/emboj.2012.15.
Linder, M. E. et al. "Palmitoylation: Policing protein stability and traffic." Nature Reviews Molecular Cell Biology 8:74-84 (2007). doi:10.1038/nrm2084.
Mabrey, S. et al. "Investigation of phase transitions of lipids and lipid mixtures by sensitivity differential scanning calorimetry." Proc. Natl. Acad. Sci. 73(11). 3862-3868 (1976). doi:10.1073/pnas.73.11.3862.
Menon, A. K. "Lipid modifications of proteins." in 'Biochemistry of Lipids, Lipoproteins and Membranes' 39-53 (2008). doi: 10.1016/B978-044453219-0.50004-0.
Myhill, N. et al. "The subcellular distribution of calnexin is mediated by PACS-2." Mol. Biol. Cell 19:2777-2788 (2008). doi:10.1091/mbc.E07-10-0995.
Revelo, N. H. et al. "A new probe for super-resolution imaging of membranes elucidates trafficking pathways." J. Cell Biol. 205(4):591-606 (2014). doi:10.1083/jcb.201402066.
Sarrazin, S. et al., "Heparan sulfate proteoglycans." Cold Spring Harb. Perspect. Biol. 2011;3:a004952. doi:10.1101/cshperspect.a004952.
Scicchitano, M. S., et al. "Protein extraction of formalin-fixed, paraffin-embedded tissue enables robust proteomic profiles by mass spectrometry." J. Histochem. Cytochem. 57(9): 849-860 (2009). doi:10.1369/jhc.2009.953497.
Seifert, U. "Configurations of fluid membranes and vesicles." Adv. Phys. 46(1):13-137 (1997). doi:10.1080/00018739700101488.
Shen, K., et al. "Comparison of different buffers for protein extraction from formalin-fixed and paraffin-embedded tissue specimens." PLoS One 10(11): e0142650 (2015). doi:10.1371/journal.pone.0142650.
Shi, S. R. et al. "Antigen retrieval in formalin-fixed, paraffin-embedded tissues: An enhancement method for immunohistochemical staining based on microwave oven heating of tissue sections." J. Histochem. Cytochem 39 (6):741-8 (1991) doi:10.1177/39.6.1709656.
Tanca, A. et al. "Comparability of differential proteomics data generated from paired archival fresh-frozen and formalin-fixed samples by GeLC-MS/MS and spectral counting," J. Proteomics 77:561-576 (2012). doi:10.1016/j.jprot.2012.09.033.
Tanca, A. et al. "Critical comparison of sample preparation strategies for shotgun proteomic analysis of formalin-fixed, paraffin-embedded samples: Insights from liver tissue." Clin. Proteomics 11:28 (2014), doi:10.1186/1559-0275-11-28.
Testagrossa et al. "Immunohistochemical expression of podocyte markers in the variants of focal segmental glomerulosclerosis." National Dial Transplant 28: 91-98 (2013).
Valenzuela, J. I. et al. "Diversifying the secretory routes in neurons." Frontiers in Neuroscience 9:358 (2015). doi:10.3389/fnins.2015.00358.
Van Meer. G., et al. "Membrane lipids: Where they are and how they behave." Nature Reviews Molecular Cell Biology 9(2): 112-124 (2008). doi:10.1038/nrm2330.
Wassie. A. T., et al. "Expansion microscopy: principles and uses in biological research." Nature Methods 16(1): 33-41 (2019). doi: 10.1038/s41592-018-0219-4.
Weber, P. C., et al. "Structural origins of high-affinity biotin binding to streptavidin." Science 243(4887):85-88 (1989). doi: 10.1126/science.2911722.
Wen, G. et al. "Evaluation of direct grafting strategies in Expansion Microscopy," BioRxiv preprint Jul. 8, 2019, doi: https://doi.org/10.1101/696039 (Jul. 8, 2019).
Wurm, C. A. et al. "Nanoscale distribution of mitochondrial import receptor Tom20 is adjusted to cellular conditions and exhibits an inner-cellular gradient." Proc. Natl. Acad. Sci. U. S. A. 108(33):13546-13551 (2011). doi:10.1073/pnas.1107553108.
Yan, B. X. et al. "Glycine residues provide flexibility for enzyme active sites." J Biol. Chem. 272(6): 3190-4 (1997). doi:10.1074/jbc.272.6.3190.

(56) References Cited

OTHER PUBLICATIONS

Zhao, Y. et al. "Nanoscate imaging of clinical specimens using pathology-optimized expansion microscopy." Nat. Biotechnol. 35(8): 757-764 (2017). doi:10.1038/nbt.3892.
Zuiderveld, K. "Contrast Limited Adaptive Histogram Equalization." in Graphics Gems 474-485 (1994). doi:10.1016/b978-0-12-336156-1.50061-6.
Chen, X et al. [Supplementary material] "AT AC-see reveals the accessible genome by transpasase-mediated imaging and sequencing," Nature Methods, vol. 13, No. 12, Oct. 17, 2016, 1813-1828.

* cited by examiner

Brain Tumor - Glioblastoma

MULTIPLEXED EXPANSION (MULTIEXM) PATHOLOGY

RELATED APPLICATION

This application claims the benefit of U.S. Provisional Application No. 62/944,195, filed on Dec. 5, 2019. The entire teachings of the above application are incorporated herein by reference.

BACKGROUND

In pathology, examination of cellular structures and molecular composition using diffraction-limited microscopy has long been key to the diagnosis of a wide variety of pre-disease and disease states. Biomolecules themselves, however, are nanoscale in dimension and configured with nanoscale precision throughout cells and tissues. In basic science, this has begun to be explored using pioneering super-resolution microscopy methods, as well as electron microscopy methods, but such strategies require complex hardware, can present a steep learning curve, and are difficult to apply to large-scale samples such as human tissues. Accordingly, super-resolution imaging and nanoscopy have not found routine utility in the clinical practice of pathology.

Thus, there is a need for higher resolution microscopy that can work with current diffraction limited microscopes and can optically magnify samples, such as tissue sections or tumors, with nanoscale precision.

SUMMARY OF THE INVENTION

The invention provides a method for preparing an expanded biological specimen. The expanded biological specimen is suitable for microscopic analysis. By "microscopic analysis" it is meant the analysis of a specimen using any technique that provides for the visualization of aspects of a specimen that cannot be seen with the unaided eye, i.e., that are not within the resolution range of the normal eye.

By "preparing an expanded biological specimen" it is generally meant that the biological specimen is physically expanded, or enlarged, relative to the specimen prior to be exposed to the method(s) described herein. Expanding the biological sample can be achieved by permeating the sample with a swellable polymer anchoring biomolecules within the sample to a polymer and swelling, or expanding, the polymer, thereby moving the biomolecules apart as further described below. As biomolecules are anchored to the polymer network isotropic expansion of the polymer retains the spatial orientation of the biomolecules resulting in an expanded, or enlarged, biological specimen.

In one embodiment, the method for preparing an expandable biological specimen comprises the steps of contacting the sample with macromolecules that will bind to biomolecules within the sample; treating the specimen with a bifunctional crosslinker; permeating the specimen with precursors of a swellable polymer; polymerizing the precursors to form a swellable polymer within the specimen; anchoring the biomolecules to the swellable polymer; and incubating the sample with 20% w/v of a detergent in a buffer having a pH between about 4 and about 12, the buffer comprising about 5 mM to about 100 mM of a metal ion chelator; about 0.1% to about 0.5-1.0% of a nonionic surfactant. The expandable biological specimen can be expanded by contacting the swellable polymer with a solvent or liquid to cause the swellable polymer to swell. In one embodiment, prior to the treating step, the sample is heat treated. By "heat treated" it is generally meant any suitable antigen retrieval process known to one of skill in the art and as further described below.

In one embodiment, the method for preparing an expandable biological specimen comprises the steps of treating the specimen with a bifunctional crosslinker; permeating the specimen with precursors of a swellable polymer; polymerizing the precursors to form a swellable polymer within the specimen; and incubating the specimen with 20% w/v of a detergent in a buffer having a pH between about 4 and about 12, the buffer comprising about 5 mM to about 100 mM of a metal ion chelator; about 0.1% to about 1.0% of a nonionic surfactant, and antioxidant in the range 10-100 mM. In one embodiment, the method can further comprise the step contacting the sample with macromolecules that will bind to biomolecules within the sample. In one embodiment, the method can further comprise the step anchoring the biomolecules to the swellable polymer. The expandable specimen can be expanded by contacting the swellable polymer with a solvent or liquid to cause the swellable polymer to swell. In one embodiment, prior to the treating step, the sample is treated with any suitable antigen retrieval process such as autoclave at 120 C for 1 hour and known to one of skill in the art and as further described below.

In one embodiment, the method for expanding a swellable material-embedded biological specimen, as further described below, comprises incubating the specimen with 20% w/v of a detergent in a buffer having a pH between about 4 and about 12, the buffer comprising about 5 mM to about 100 mM of a metal ion chelator; about 0.1% to about 1.0% of a nonionic surfactant, and antioxidant in the range 10-100 mM, and contacting the swellable polymer with a solvent or liquid to cause the swellable polymer to swell. In one embodiment, prior to the treating step, the sample is treated with a collagenase enzyme solution in the range 300-1200 U/ml at 37 C temperature for 1-6 hrs in a Hanks Balance Salt Solution buffer with calcium. In one embodiment, prior to the treating step, the sample is treated with any suitable antigen retrieval process known to one of skill in the art and as further described below.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

Post-expansion images in FIG. 1E-G acquired with a spinning disc confocal microscope of same area as FIG. 1A-C. DAPI, (FIG. 1A); MAP2, (FIG. 1B). RMS length measurement error as a function of measurement length for post-expansion vs pre-expansion SR-SIM images of normal human brain tissues in FIG. 1D dark line, mean of DAPI channel; FIG. 1P dark line, mean of vimentin channel; shaded area s.e.m.; n=3 samples from different patients. Scale bars: FIG. 1A-C, and FIG. 1I-K) Sum.

FIG. 2A, D 5 µm; FIG. 2B-C and FIG. 2E-F 20 µm; inset 1 µm pre-expansion, 4 µm post-expansion.

FIGS. 3A, 3D, and 3G show baseline images prior to incubation in stripping buffer. FIGS. 3B, 3E, and 3H post-stripping images after 135 min incubation in stripping buffer. FIGS. 3C, 3F, and 3I show fluorescence signal decay graphs for each channel; for each channel n=3 tissue microarray cores with 3 areas per core and 5 regions of interest of 221 µm². All post stripping time points were registered to the baseline DAPI images using an automated SIFT registration algorithm. Repeated measure anova with Bonferroni correction analysis was performed (***$p<0.001$ otherwise not significant).

FIG. 4 Post-expansion zoomed in images of normal human hippocampus at vascular interface delineating FIG. 4A nuclei (DAPI), FIG. 4B-C myelin basic protein (rabbit antibody; chicken antibody; FIG. 4D astrocytes (GFAP) and FIG. 4E composite image of FIG. 4A-D and FIG. 4F neuronal microtubule marker (beta-III-tubulin); FIG. 4G neuronal dendritic marker (MAP2); FIG. 4H microtubule marker (alpha-tubulin); FIG. 4I neurofilament marker (NF70); FIG. 4J composite of FIG. 4F-L and FIG. 4K intermediate filament marker (desmin); FIG. 4L synaptic marker (synapsin-1); FIG. 4M astrocytic filament marker (Sl00beta); and FIG. 4N pericyte marker (alpha-SMA); FIG. 4O composite of FIG. 4K-N. Zoomed in areas marked by white box at bottom of figure shown in inset on upper right corner of images. Scale bars in post-expansion images indicate 20 µm and 5 µm in pre-expansion images); inset 8 µm (2 nm pre-expansion).

FIG. 5A DAPI; FIG. 5B collagen;

FIG. 5C vimentin; FIG. 5D GFAP; FIG. 5E mitochondrial marker Tomm20; FIG. 5F von willebrand factor; FIG. 5G proliferation marker Ki-67; FIG. 5H composite image. Zoomed in areas marked by white box at top of figure shown in inset on bottom right corner of images. (Scale bars in post-expansion images indicate 20 µm and 5 µm in pre-expansion images); inset 2 µm (500 nm pre-expansion).

DETAILED DESCRIPTION

Figure 1A:
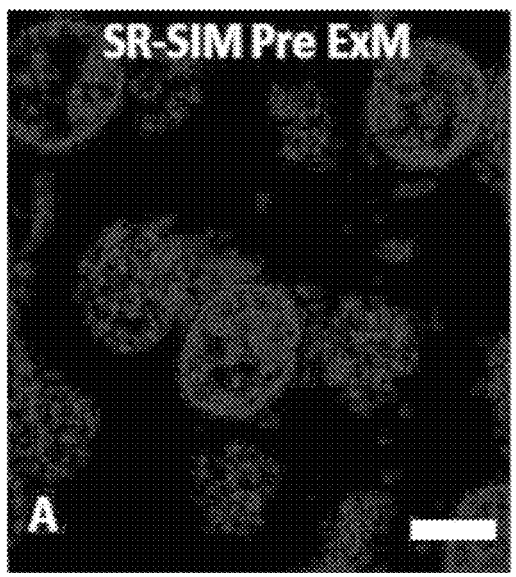
FIG. 1A through FIG. 1P Validation of Multiplexed ExM of Normal Brain and Brain Tumors. Pre-expansion images in FIG. 1A-C of a tissue microarray core of normal human hippocampus acquired with a super-resolution structured illumination microscope (SR-SIM).
Figure 1B:
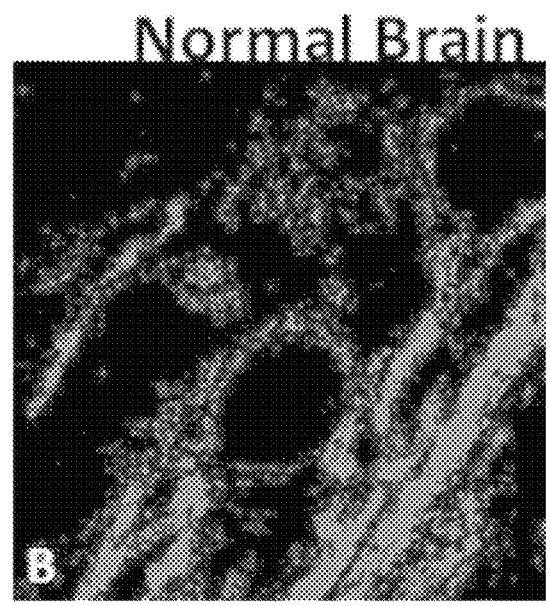
Figure 1C:
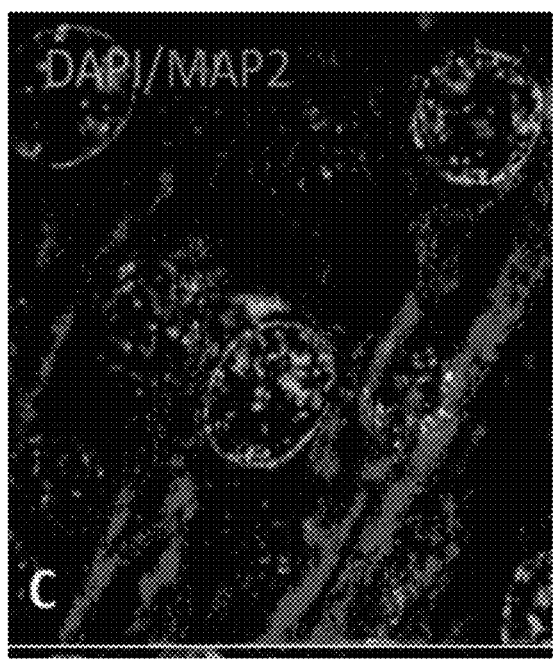
Figure 1D:
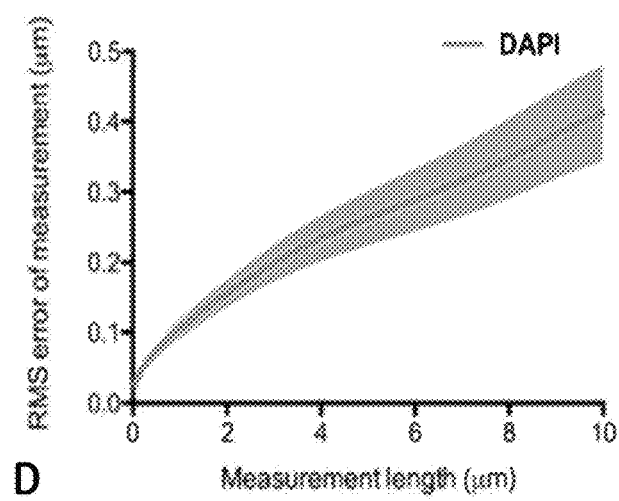
Figure 1E:
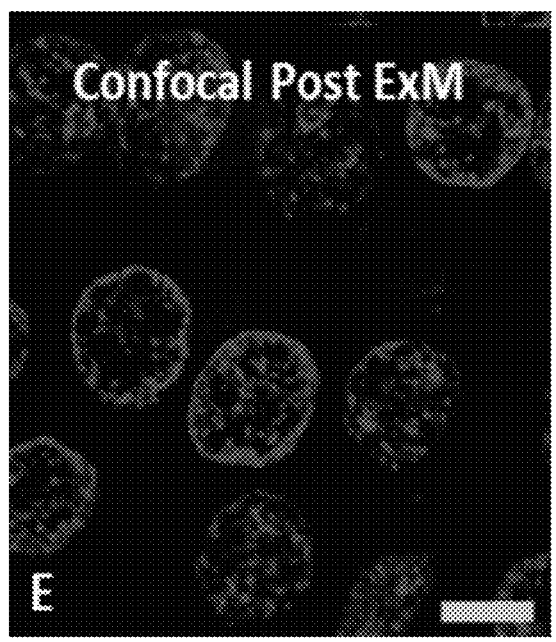
FIG. 1E-G, FIG. 1M-O) 20 µm.
Figure 1F:
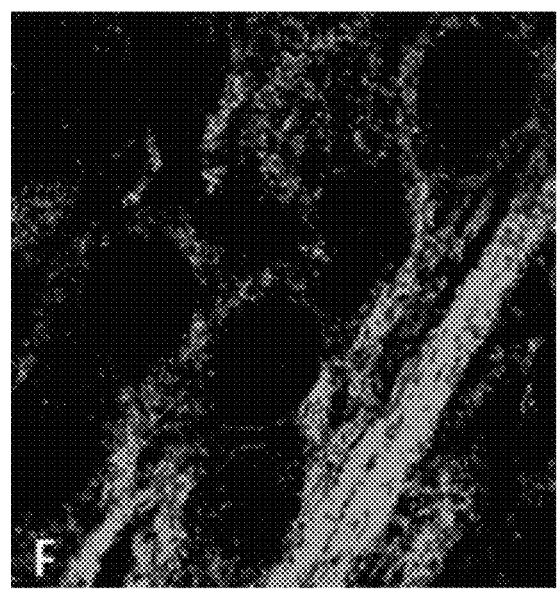
Figure 1G:
Figure 1H:
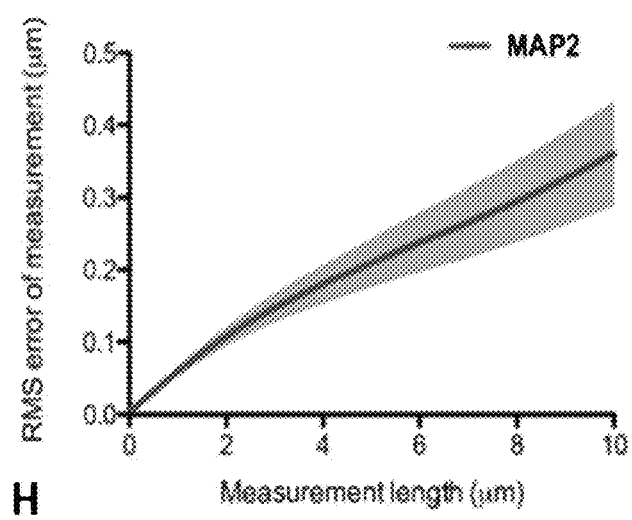
FIG. 1H dark line, mean of MAP2 channel: shaded area s.e.m.; n=4 samples from different patients. Pre-expansion images in FIG. 1I-K of a tissue microarray core of human glioblastoma acquired with SR-SIM. Post-expansion images in FIG. 1M-O acquired with a spinning disc confocal microscope of same area as FIG. 1I-K. DAPI, FIG. 1I; vimentin, FIG. 1K. RMS length measurement error as a function of measurement length for post-expansion vs pre-expansion SR-SIM images of human glioblastoma tissues in FIG. 1L and FIG. 1P (FIG. 1L dark line, mean of DAPI channel.
Figure 1I:
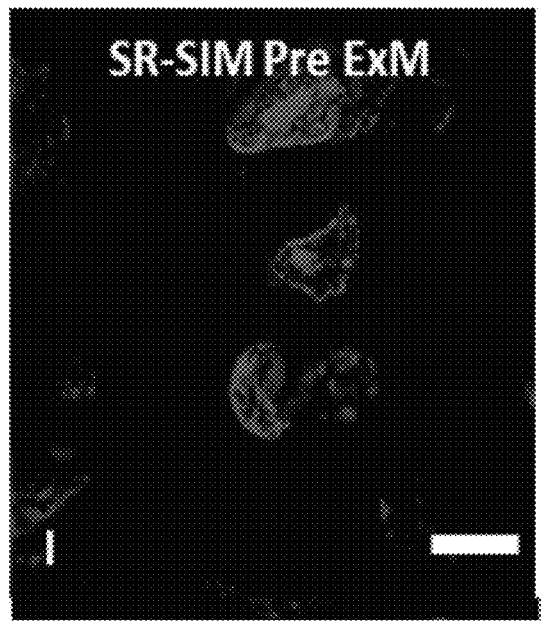
Figure 1J:
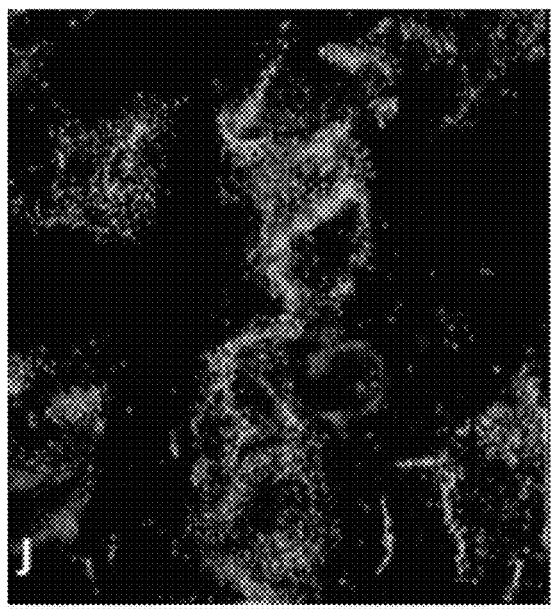
Figure 1K:
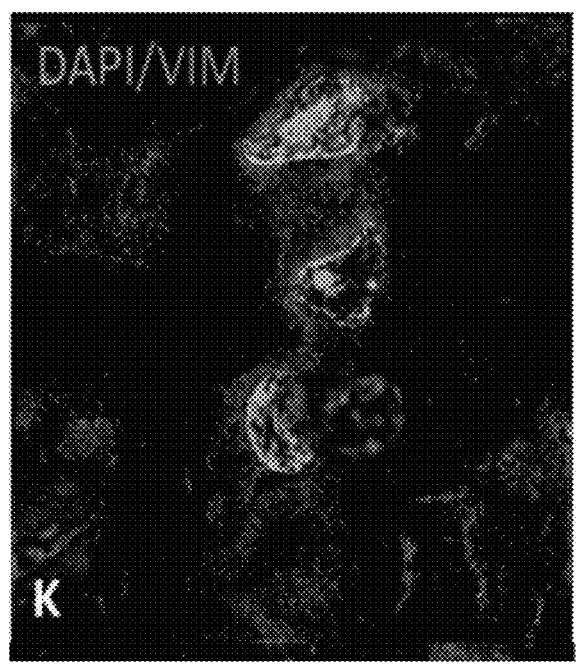
Figure 1L:
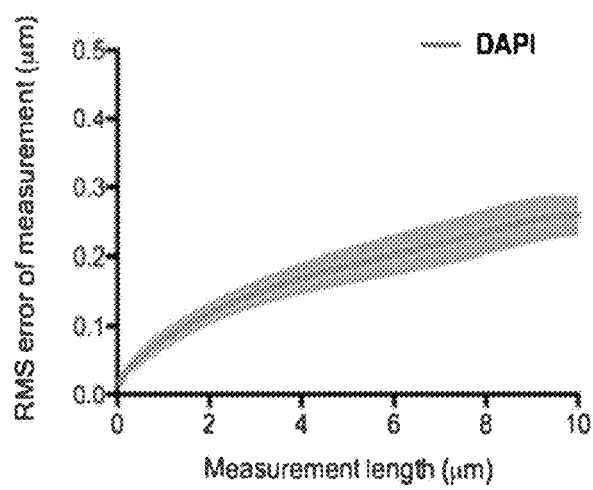
Figure 1M:
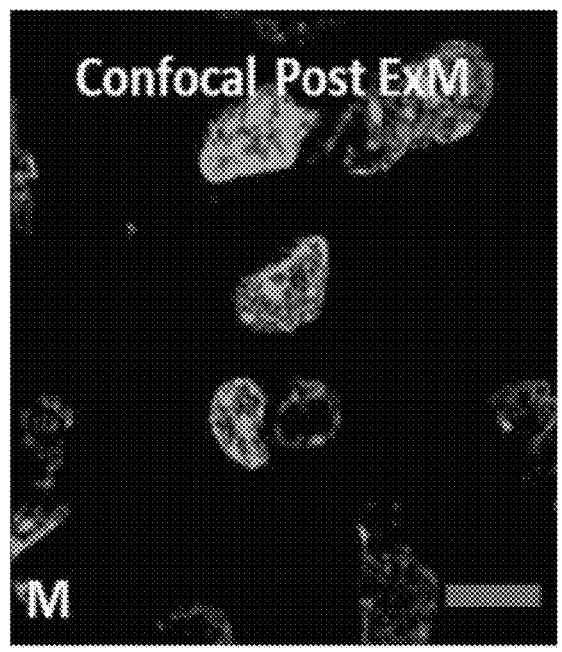
Figure 1N:
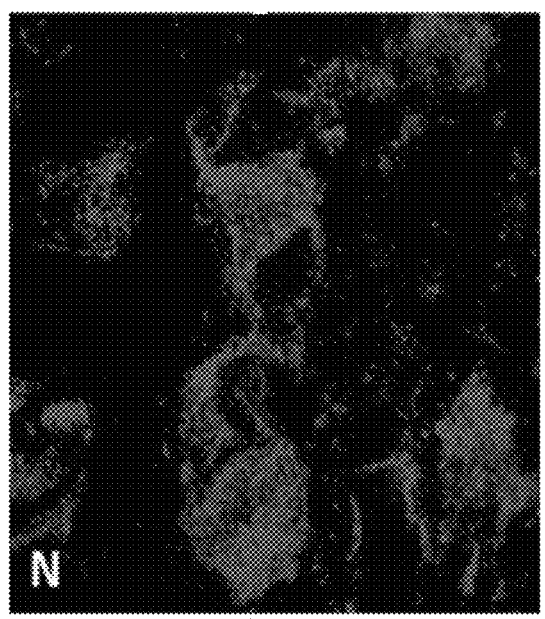
Figure 1O:
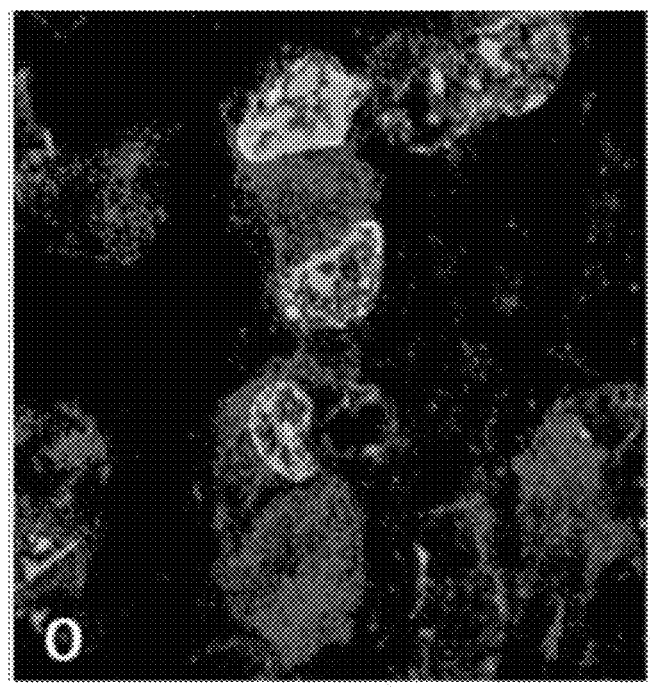
Figure 1P:
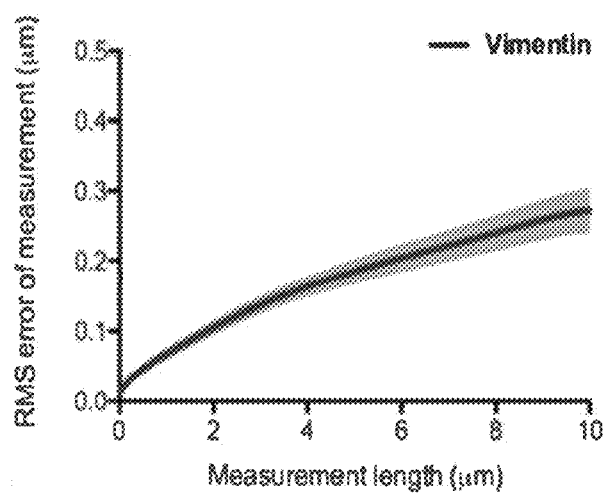

The invention provides expansion pathology (ExPath), a simple and versatile method for optical interrogation of biological samples, e.g., clinical biopsy samples, with nanoscale precision and molecular identity. ExPath is capable of processing the majority of clinical samples currently used in pathology including formalin-fixed paraffin-embedded (FFPE), hematoxylin and eosin (H&E)-stained, and/or fresh frozen tissue specimens and thus enables nanoscale imaging without the need for hardware beyond that found in conventional laboratories. ExPath functions well on a wide diversity of tissue types, and has immediate clinical application in the diagnosis of diseases known to exhibit nanoscale pathology.

As used herein and in the appended claims, the singular forms "a", "an", and "the" are defined to mean "one or more" and include the plural unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation. As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

The invention provides a method for preparing an expanded biological specimen. The expanded biological specimen is suitable for microscopic analysis. By "microscopic analysis" it is meant the analysis of a specimen using any technique that provides for the visualization of aspects of a specimen that cannot be seen with the unaided eye, i.e., that are not within the resolution range of the normal eye.

By "preparing an expanded biological specimen" it is generally meant that the biological specimen is physically expanded, or enlarged, relative to the specimen prior to be exposed to the method(s) described herein. Expanding the biological sample can be achieved by anchoring biomolecules within the sample to a polymer network and swelling, or expanding, the polymer network, thereby moving the biomolecules apart as further described below. As the biomolecules are anchored to the polymer network isotropic expansion of the polymer network retains the spatial orientation of the biomolecules resulting in an expanded, or enlarged, biological specimen.

In one embodiment, the method for preparing an expandable biological specimen comprises the steps of contacting the sample with macromolecules that will bind to biomolecules within the sample; treating the specimen with a bifunctional crosslinker; permeating the specimen with precursors of a swellable polymer; polymerizing the precursors to form a swellable polymer within the specimen; anchoring the biomolecules to the swellable polymer; and incubating the sample with a detergent in a buffer comprising a metal ion chelator, and a non-ionic surfactant. In one embodiment, the method comprises incubating the specimen with about 20% w/v detergent in a buffer having a pH between about 4 and about 12, the buffer comprising about 5 mM to about 100 mM of a metal ion chelator; about 0.1% to about 1.0% of a nonionic surfactant, and antioxidant in the range 10-100 nmM. In one embodiment, the sample is incubated for about 1-2 hrs at 120° C. in an autoclave.

The expandable biological specimen can be expanded by contacting the swellable polymer with a solvent or liquid to cause the swellable polymer to swell.

In one embodiment, prior to the contacting step, the sample is subjected to any suitable antigen retrieval process known to one of skill in the art and as further described below.

In one embodiment, the method for preparing an expandable biological specimen comprises the steps of treating the specimen with a bifunctional crosslinker: permeating the specimen with precursors of a swellable polymer; polymerizing the precursors to form a swellable polymer within the specimen; and incubating the specimen with detergent in a buffer comprising a metal ion chelator, a nonionic surfactant. In one embodiment, the method can further comprise the step contacting the sample with macromolecules that will bind to biomolecules within the sample. In one embodiment, the method can further comprise the step anchoring the biomolecules to the swellable polymer. In one embodiment, the method comprises incubating the specimen with about 20% w/v detergent in a buffer having a pH between about 4 and about 12, the buffer comprising about 5 mM to about 100 mM of a metal ion chelator; about 0.10% to about 1.0% of a nonionic surfactant, and antioxidant in the range 10-100 mM.

The expandable specimen can be expanded by contacting the swellable polymer with a solvent or liquid to cause the swellable polymer to swell.

In one embodiment, prior to the treating step, the sample is treated with a collagenase enzyme solution in the range 300-1200 U/ml at 37 C temperature for 1-6 hours in a Hanks Balance Salt Solution buffer with calcium, and any suitable antigen retrieval process known to one of skill in the art and as further described below.

In one embodiment, the invention provides a method for expanding a biological specimen embedded in a swellable material. In one embodiment the specimen is a swellable material-embedded biological specimen as further described herein. The method comprises incubating the specimen with a detergent in a buffer comprising a metal ion chelator, a nonionic surfactant; and contacting the swellable polymer with a solvent or liquid to cause the swellable polymer to swell. In one embodiment, the method comprises incubating the specimen with about 20% w/v of a detergent in a buffer having a pH between about 4 and about 12, the buffer comprising about 5 mM to about 100 mM of a metal ion chelator; about 0.1% to about 1.0% of a nonionic surfactant, and antioxidant in the range 10-100 mM.

The terms "biological specimen" or "biological sample" is used herein in a broad sense and is intended to include sources that contain nucleic acids and can be fixed. Exemplary biological samples include, but are not limited to, tissues of the central nervous system. Other exemplary biological samples include cells, liquid samples. Materials obtained from clinical or forensic settings are also within the intended meaning of the term biological sample. In one embodiment, the sample is derived from a human, animal or plant. In one embodiment, the biological sample is a tissue sample, preferably an organ tissue sample. In one embodiment, samples are human. The sample can be obtained, for example, from autopsy, biopsy or from surgery. It can be a solid tissue such as, for example, parenchyme, connective or fatty tissue, heart or skeletal muscle, smooth muscle, skin, brain, nerve, kidney, liver, spleen, breast, carcinoma (e.g. bowel, nasopharynx, breast, lung, stomach etc.), cartilage, lymphoma, meningioma, placenta, prostate, thymus, tonsil, umbilical cord or uterus. The tissue can be a tumor (benign or malignant), cancerous or precancerous tissue. The sample can be obtained from an animal or human subject affected by disease or other pathology or suspected of same (normal or diseased) or considered normal or healthy. As used herein, the term "fixed biological sample, explicitly excludes cell-free samples, for example cell extracts, wherein cytoplasmic and/or nuclear components from cells are isolated.

Tissue specimens suitable for use with the methods and systems described herein generally include any type of tissue specimens collected from living or dead subjects, such as, e.g., biopsy specimens and autopsy specimens. Tissue specimens may be collected and processed using the methods and systems described herein and subjected to microscopic analysis immediately following processing or may be preserved and subjected to microscopic analysis at a future time, e.g., after storage for an extended period of time. In some embodiments, the methods described herein may be used to preserve tissue specimens in a stable, accessible and fully intact form for future analysis. For example, tissue specimens, such as, e.g., human brain tissue specimens, may be processed as described above and cleared to remove a plurality of cellular components, such as, e.g., lipids, and then stored for future analysis.

Tissues that have been preserved, or fixed, contain a variety of chemical modifications that can reduce the detectability of proteins in biomedical procedures. In some embodiments, the methods and systems described herein may be used to analyze a previously-preserved or stored tissue specimen. Previously preserved tissue specimens include, for example, clinical samples used in pathology including formalin-fixed paraffin-embedded (FFPE), hematoxylin and eosin (H&E)-stained, and/or fresh frozen tissue specimens. If the previously preserved sample has a coverslip, the coverslip should be removed. The sample is treated to remove the mounting medium. Such methods for removing the mounting medium are well known in the art. For example, treating the sample with xylene to remove paraffin or other hydrophobic mounting medium. Alternatively, if the sample is mounted in a water-based mounting medium, the sample is treated with water. The sample is then then rehydrated and subjected to antigen-retrieval. The term "antigen retrieval" refers to any technique in which the masking of an epitope is reversed and epitope-antibody binding is restored such as, but not limited to, enzyme induced epitope retrieval, heat induced epitope retrieval (HIER), or proteolytic induced epitope retrieval (PIER). For example, the antigen retrieval treatment can be performed in a 10 mM sodium citrate buffer as well as the commercially available Target Retrieval Solution (DakoCytomation) or such.

By "biomolecules" it is generally meant, but not limited to, proteins, lipids, steroids, nucleic acids, and sub-cellular structures within a tissue or cell.

By "macromolecules" is meant proteins, nucleic acids, or small molecules that target biomolecules within the specimen. These macromolecules are used to detect biomolecules within the specimen and/or anchor the biolmolecules to the swellable polymer. For example, macromolecules may be provided that promote the visualization of particular cellular biomolecules, e.g., proteins, lipids, steroids, nucleic acids, etc. and sub-cellular structures. In some embodiments, the macromolecules are diagnostic. In some embodiments, the macromolecules are prognostic. In some embodiments, the macromolecules are predictive of responsiveness to a therapy. In some embodiments, the macromolecules are candidate agents in a screen, e.g., a screen for agents that will aid in the diagnosis and/or prognosis of disease, in the treatment of a disease, and the like.

As an example, the specimen may be contacted with one or more polypeptide macromolecules, e.g. antibodies, labeled peptides, and the like, that are specific for and will bind to particular cellular biomolecules for either direct or indirect labeling by color or immunofluorescence. By immunofluorescence it is meant a technique that uses the highly specific binding of an antibody to its antigen or binding partner in order to label specific proteins or other molecules within the cell. A sample is treated with a primary antibody specific for the biomolecule of interest. A fluorophore can be directly conjugated to the primary antibody or peptide. Alternatively, a secondary antibody, conjugated to a detection moiety or fluorophore, which binds specifically to the first antibody can be used. Peptides that are specific for a target cellular biomolecule and that are conjugated to a fluorophor or other detection moiety may also be employed.

Another example of a class of agents that may be provided as macromolecules is nucleic acids. For example, a specimen may be contacted with an antisense RNA that is complementary to and specifically hybridizes to a transcript of a gene of interest, e.g., to study gene expression in cells of the specimen. As another example, a specimen may be contacted with a DNA that is complementary to and specifically hybridizes to genomic material of interest, e.g., to study genetic mutations, e.g., loss of heterozygosity, gene duplication, chromosomal inversions, and the like. The hybridizing RNA or DNA is conjugated to detection moieties, i.e. agents that may be either directly or indirectly visualized microscopically. Examples of in situ hybridization techniques may be found at, for example, Harris and Wilkinson. In situ hybridization: Application to developmental biology and medicine, Cambridge University Press 1990; and Fluorescence In Situ Hybridization (FISH) Application Guide. Liehr, T, ed., Springer-Verlag, Berlin Heidelberg 1990.

In one embodiment, the biological sample can be labeled or tagged with a detectable label. Typically, the label or tag will bind chemically (e.g., covalently, hydrogen bonding or ionic bonding) to a biomolecule of the sample, or a component thereof. The detectable label can be selective for a specific target (e.g., a biomarker or class of molecule), as can be accomplished with an antibody or other target specific binder. The detectable label may comprise a visible component, as is typical of a dye or fluorescent molecule; however any signaling means used by the label is also contemplated. A fluorescently labeled biological sample, for example, is a biological sample labeled through techniques such as, but not limited to, immunofluorescence, immunohistochemical or immunocytochemical staining to assist in microscopic analysis. In one embodiment, the detectable label is chemically attached to the biological sample, or a targeted component thereof. In one embodiment, the detectable label is an antibody and/or fluorescent dye wherein the antibody and/or fluorescent dye, further comprises a physical, biological, or chemical anchor or moiety that attaches or crosslinks the specimen to the swellable polymer, such as a swellable hydrogel. The labeled sample may furthermore include more than one label. For example, each label can have a particular or distinguishable fluorescent property, e.g., distinguishable excitation and emission wavelengths. Further, each label can have a different target specific binder that is selective for a specific and distinguishable target in, or component of the sample.

As used herein a bifunctional crosslinker comprises a reactive group to functional groups (e.g., primary amines or sulfhydryls) on biomolecules within the sample and a swellable material reactive group.

The bifunctional crosslinker is used to chemically modify the functional group of biomolecules with a swellable polymer functional group, which enables antibodies and other endogenous biomolecules within the sample to be directly anchored to, or incorporate into, the swellable polymer. In one embodiment, the bifunctional crosslinker is a hetero-bifunctional crosslinker. Hetero-bifunctional crosslinkers possess different reactive groups at either end of a spacer arm, i.e., atoms, spacers or linkers separating the reactive groups. These reagents not only allow for single-step conjugation of molecules that have the respective target functional group, but they also allow for sequential (two-steps) conjugations that minimize undesirable polymerization or self-conjugation. The bifunctional crosslinker may be a small molecule linker or a nucleic acid adaptor.

As used herein, a "nucleic acid adaptor" is a nucleic acid sequence having a binding moiety capable of attaching to a target nucleic acid and an anchor moiety capable of attaching to the swellable material. Attaching the nucleic acid adaptor to a target nucleic acid may be accomplished by hybridization or by ligation in situ. For example, DNA adaptors may be ligated to the 3' ends of the RNAs in the sample with RNA ligases, such as T4 RNA ligase, or may be attached via a chemical linker such as a reactive amine group capable of reacting with target nucleic acid. Acrylamide modified oligonucleotide primers may be covalently fixed within a swellable material such as a polyacrylate gel. As used herein, the term "acrylamide modified" in reference to an oligonucleotide means that the oligonucleotide has an acrylamide moiety attached to the 5' end of the molecule.

As used herein, a "small molecule linker" is a small molecule having a binding moiety capable of attaching to a target nucleic acid and an anchor moiety capable of attaching to the swellable material. Attaching the small molecule linker to the target nucleic acid may be accomplished by hybridization or by a chemical reactive group capable of covalently binding the target nucleic acid. For example, LABEL-IT® Amine (MirusBio) is a small molecule with alkylating group that primarily reacts to the N7 of guanine, thereby allowing covalent binding of RNA and DNA. The small molecule linker may be, for example, acrylamide modified and therefore may be covalently fixed within a swellable material. As used herein, the term "acrylamide modified" in reference to a small molecule linker means that the small molecule linker has an acrylamide moiety.

In one embodiment, the bifinctional crosslinker comprises a protein-reactive chemical moiety and a swellable material-reactive chemical moiety (i.e., a swellable polymer-reactive chemical moiety). The protein-reactive chemical group includes, but is not limited to, N-hydroxysuccinimide (NHS) ester, thiol, amine, maleimide, imidoester, pyridyldithiol, hydrazide, phthalimide, diazirine, aryl azide, isocyanate, or carboxylic acid, which, for example, can be reacted with amino or carboxylic acid groups on proteins or peptides. In one embodiment, the protein-reactive groups include, but are not limited to, N-succinimidyl ester, pentafluorophenyl ester, carboxylic acid, or thiol. The swellable material-reactive groups include, but are not limited to, vinyl or vinyl monomers such as styrene and its derivatives (e.g., divinyl benzene), acrylamide and its derivatives, butadiene, acrylonitrile, vinyl acetate, or acrylates and acrylic acid derivatives.

In one embodiment, the chemical to anchor proteins directly to any swellable polymer is a succinimidyl ester of 6-((acryloyl)amino)hexanoic acid (acryloyl-X, SE; abbreviated "AcX"; Life Technologies). Treatment with AcX modifies amines on proteins with an acrylamide functional group. The acrylamide functional groups allows for proteins to be anchored to the swellable polymer as it is synthesized in situ.

In one embodiment, the proteins of the sample of interest can be modified with the protein-reactive group and the swellable material-reactive group in separate steps using click chemistry. Click chemistry, also referred to as tagging, is a class of biocompatible reactions intended primarily to join substrates of choice with specific biomolecules. In this method, proteins of the sample of interest are treated with a protein-reactive group comprising a click group and then treated with a swellable material-reactive group comprising a complementary click group. Complementary groups include, but are not limited to, azide groups and terminal alkynes (see e.g., H. C. Kolb; M G. Finn; K. B. Sharpless (2001). "*Click Chemistry: Diverse Chemical Function from a Few Good Reactions*". Angewandte Chemie International Edition. 40(11): 2004-2021, which is incorporated herein by reference).

As used herein, the term "attach" or "attached" refers to both covalent interactions and noncovalent interactions. In certain embodiments of the invention, covalent attachment may be used, but generally all that is required is that the bi-functional linker remain attached to the biomolecules. Attachment can occur via hybridization to the biomolecules. The term "attach" may be used interchangeably herein with the terms, "anchor(ed)", affix(ed), link(ed) and immobilize (d).

The biological specimen is embedded in a swellable material. As used herein, the terms "swellable material" and "swellable polymer" are used interchangeably and generally refers to a material that expands when contacted with a liquid, such as water or other solvent, or dilute salt solutions such as phosphate buffered saline. In some embodiments, the swellable material uniformly expands in three dimensions. Additionally or alternatively, the material is transparent such that, upon expansion, light can pass through the sample. The first swellable material and the second swellable material may be the same or different swellable materials.

In one embodiment, the swellable material is formed in situ from precursors thereof. Embedding the sample in the swellable material comprises permeating the sample with a composition comprising one or more precursors thereof throughout the sample and polymerizing and/or crosslinking the monomers or precursors to form the swellable material. In this manner the sample of interest is embedded in the swellable material.

In one embodiment, the sample of interest and each iteratively enlarged sample is permeated with one or more monomers or precursors or a solution comprising one or more monomers or precursors which are then reacted to form a swellable or non-swellable material depending on what step of the method is being performed.

By "precursors of a swellable material" it is meant hydrophilic monomers, prepolymers, or polymers that can be crosslinked, or "polymerized", to form a three-dimensional (3D) hydrogel network. Precursors can also comprise polymerization initiators and crosslinkers.

In one embodiment the swellable material is a polyelectrolyte. In one embodiment, the swellable material is polyacrylate or polyacrylamide and copolymers or crosslinked copolymers thereof.

In some embodiments, one or more polymerizable materials, monomers or oligomers can be used, such as monomers selected from the group consisting of water soluble groups containing a polymerizable ethylenically unsaturated group. Monomers or oligomers can comprise one or more substituted or unsubstituted methacrylates, acrylates, acrylamides, methacrylamides, vinylalcohols, vinylamines, allylamines, allylalcohols, including divinylic crosslinkers thereof (e.g., N,N-alkylene bisacrylamides).

In one embodiment, the precursor of the swellable material comprises at least one polyelectrolyte monomer and a covalent crosslinker. In one embodiment, the swellable material is a hydrogel. In one embodiment, the hydrogel is a polyacrylate hydrogel. In one embodiment, the precursor of the swellable material comprises acrylate, acrylamide, and a crosslinker selected from N,N-methylenebisacrylamide (BIS), N,N'-(1,2-Dihydroxythylene)bisacryalmide) (DHEBA); and N,N'-Bis(acryloyl)cystamine (BAC).

Without being bound by scientific theory, it is believed that this fixation of the biological specimen in the presence of hydrogel subunits crosslinks the biomolecules of the specimen to the hydrogel subunits, thereby securing molecular components in place, preserving the tissue architecture and cell morphology.

The precursors of the swellable polymer may be delivered to the biological specimen by any convenient method including, but not limited to, permeating, perfusing, infusing, soaking, adding or other intermixing the sample with the precursors of swellable material. In this manner, the biological specimen is saturated with precursors of the swellable material, which flow between and around biomolecules throughout the specimen.

Following permeating the specimen, the swellable polymer precursors are polymerized to form a polymer network. The polymer network is formed within and throughout the specimen. In this manner, the biological specimen is saturated with the swellable material, which flow between and around biomolecules throughout the specimen.

Polymerization may be by any method including, but not limited to, thermal crosslinking, chemical crosslinking, physical crosslinking, ionic crosslinking, photo-crosslinking, irradiative crosslinking (e.g., x-ray, electron beam), and the like, and may be selected based on the type of hydrogel used and knowledge in the art. In one embodiment, the polymer is a hydrogel. Once polymerized, a polymer-embedded biological specimen is formed.

In this method, native proteins anchored to the swellable polymer perfused throughout the sample as described herein can retain epitope functionality and be labeled post homogenization treatments. Such approaches may overcome the limitations inherent to delivering antibodies in the crowded environment of native tissue.

By embedding a specimen in a swellable polymer that physically supports the ultrastructure of the specimen this technology preserves the biomolecules (e.g., proteins, small peptides, small molecules, and nucleic acids in the specimen) in their three-dimensional distribution, secured by the polymer network. By bypassing destructive sectioning of the specimen, subcellular structures may be analyzed. In addition, the specimen can be iteratively stained, unstained, and restained with other reagents for comprehensive analysis.

After the biological sample has been anchored to the swellable polymer, the specimen is subjected to a disruption of the endogenous biological molecules or the physical structure of the biological sample, leaving the macromolecules that preserve the information of the targeted biological molecules intact and anchored to the swellable polymer. In this way, the mechanical properties of the specimen-swellable polymer complex are rendered more spatially uniform, allowing greater and more consistent isotropic expansion.

The disruption of the endogenous physical structure of the specimen or of the endogenous biological molecules of the biological specimen generally refers to the mechanical, physical, chemical, biochemical or enzymatic digestion, disruption or break up of the sample so that it will not resist expansion. In one embodiment, a detergent is used to homogenize the sample-swellable polymer complex.

In one embodiment, the detergent is in a buffer having a pH from about 4 to about 12. Any suitable buffer agent can be used including, but not limited to, Tris, citrate, phosphate, bicarbonate, MOPS, borate, TAPS, bicine, Tricine, HEPES, TES, and MES.

In one embodiment, the buffer comprises a detergent, a metal ion chelator, a nonionic surfactant. In one embodiment, the buffer comprises about 20% w/v of a detergent in a buffer having a pH between about 4 and about 12, the buffer comprising about 5 mM to about 100 mM of a metal ion chelator; about 0.1% to about 1.0% of a nonionic surfactant, and antioxidant in the range 10-100 mM. In one embodiment, the sample is incubated in the buffer for about 1-2 hrs at 120 C in an autocalve. In one embodiment, the buffer comprises about 20% w/v of a detergent in a buffer having a pH between about 4 and about 12, the buffer comprising about 5 mM to about 100 mM of a metal ion chelator; about 0.10% to about 1.0% of a nonionic surfactant, and antioxidant in the range 10-100 mM.

In one embodiment, prior to the detergent treating step, the sample is treated with a collagenase enzyme solution in the range 300-1200 U/ml at 37 C temperature for 1-6 hrs in a Hanks Balance Salt Solution buffer with calcium, and any suitable antigen retrieval process known to one of skill in the art and as further described below. Subsequently, samples are treated using a buffer comprises about 20% w/v of a detergent in a buffer having a pH between about 4 and about 12, the buffer comprising about 5 mM to about 100 mM of a metal ion chelator; about 0.1% to about 1.0% of a nonionic surfactant, and antioxidant in the range 10-100 mM.

Detergents are well known to those of skill in the art. Detergents include, but are not limited to, sodium dodecyl sulfate (SDS) In one embodiment, the buffer comprises about 20% of a detergent. In one embodiment, the buffer comprises about 5-20% of a detergent.

Chelating agents are well known to those of skill in the art. Chelating agents include, but are not limited to, EDTA, EGTA, EDDHA, EDDS, BAPTA and DOTA. In one embodiment the buffer comprises about 5 mM to about 100 mM of a metal ion chelator. In one embodiment the buffer comprises about 5 mM to about 75 mM of a metal ion chelator. In one embodiment the buffer comprises about 5 mM to about 50 mM of a metal ion chelator. Nonionic surfactant are well known to those of skill in the art. Nonionic surfactants include, but are not limited to, Triton X-100, Tween 20, Tween 80, Sorbitan, Polysorbate 20, Polysorbate 80, PEG, Decyl glucoside, Decyl polyglucose and cocamide DEA. In one embodiment the buffer comprises about 0.1% to about 1.0% nonionic surfactant. In one embodiment the buffer comprises about 0.1% to about 0.75% nonionic surfactant. In one embodiment the buffer comprises about 0.1% to about 0.5% nonionic surfactant. In one embodiment the buffer comprises about 0.1% to about 0.3% nonionic surfactant.

Antioxidants are well known to those of skill in the art. Antioxidants include, but are not limited to, β-mercaptoethanol, and dithiothretiol. In one embodiment, the buffer comprises about 10-100 mM of an antioxidant. In one embodiment, the antioxidant is β-mercaptoethanol.

It is preferable that the disruption does not impact the structure of the swellable polymer but disrupts the structure of the sample. Thus, the sample disruption should be substantially inert to the swellable polymer. The degree of digestion can be sufficient to compromise the integrity of the mechanical structure of the sample or it can be complete to the extent that the sample-swellable polymer complex is rendered substantially free of the sample.

The sample-swellable polymer complex is then expanded for example, by contacting the swellable polymer with a solvent or liquid which is then absorbed by the swellable polymer and causes swelling. Where the swellable polymer is water swellable, an aqueous solution can be used. The swelling of the swellable polymer results in the sample itself expanding (e.g., becoming larger). This is because the polymer is embedded throughout the sample, therefore, as the polymer swells (grows) it expands and causes the anchored biomolecules to pull apart (i.e., move away) from each. In one embodiment, the swellable polymer expands (swells) isotropically; therefore, the anchored biomolecules retain the relative spatial orientation within the sample.

The swollen biological sample-polymer complex can be imaged on any optical microscope, allowing effective imaging of features below the classical diffraction limit. Since the resultant sample can be transparent, custom microscopes capable of large volume, wide field of view, 3D scanning may also be used in conjunction with the expanded sample. The method also provides an optional step comprising amplification of the detectable label.

Using the described methods, reagents, kits, systems and devices, the ordinarily skilled artisan will be able to prepare any biological specimen for microscopic analysis. Methods, reagents, kits, systems and devices may be used to prepare a specimen from any plant or animal, including but not limited to transgenic animals, e.g., vertebrate or invertebrate, e.g. insect, worm, xenopus, zebrafish, mammal, e.g., equine, bovine, ovine, canine, feline, murine, rodent, non-human primate or human. Tissue specimens may be collected from living subjects (e.g., bipsy samples) or may be collected from dead subjects (e.g., autopsy or necrospsy samples). The specimens may be of any tissue type, e.g. hematopoietic, neural (central or peripheral), glial, mesenchymal, cutaneous, mucosal, stromal, muscle (skeletal, cardiac, or smooth), spleen, reticulo-endothelial, epithelial, endothelial, hepatic, kidney, pancreatic, gastrointestinal, pulmonary, fibroblast, and other cell types. In some instances, the specimen is the entire organism, e.g., a worm, an insect, a zebrafish. In other instances, the specimen is a whole organ, e.g., the whole brain of a rodent. In other instances, the specimen is a portion of an organ, i.e. a biopsy, e.g., a biopsy of a transplanted tissue. The specimen may be freshly isolated or preserved, e.g. snap frozen. In some embodiments, the specimen may be a previously preserved specimen, such as, e.g., a preserved specimen from a tissue bank, e.g., a preserved specimen of a human brain obtained from a tissue collection program. In some instances, a specimen may be from a subject known to suffer from a specified disease or condition, such as, e.g., a sample of brain tissue from an autistic human. In other instances, a sample may be from a "normal" subject that does not suffer from a specific disease or condition. In some instances, a sample may be from a transgenic subject, such as, e.g., a transgenic mouse.

Because the cells and/or biomolecules of the specimen are anchored to a swellable polymer that physically supports the ultrastructure of the specimen, cellular components (e.g. lipids) that normally provide structural support but that hinder visualization of subcellular proteins and molecules may be removed while preserving the 3-dimensional architecture of the cells and tissue. This removal renders the interior of biological specimen substantially permeable to light and/or macromolecules, allowing the interior of the specimen, e.g., cells and subcellular structures, to be microscopically visualized without time-consuming and disruptive sectioning of the tissue. Additionally, the specimen can be iteratively stained, unstained, and re-stained with other reagents for comprehensive analysis.

The subject methods find many uses. For example, the subject methods may be applied to preparing specimens for the study of the connectivity of the central nervous system. "Connectivity" as used herein generally means the connections between neurons, and includes connections at the single cell level, e.g., synapses, axon termini, dendritic spines, etc., as well as connections between groups of neurons and regions of the CNS as major axon tracts, e.g., corpus callosum (CC), anterior commissure (AC), hippocampal commissure (HC), pyramidal decussation, pyramidal tracts, external capsule, internal capsule (IC), cerebral peduncle (CP), etc. A whole brain and/or spinal cord specimen or region thereof (e.g., cerebrum (i.e., cerebral cortex), cerebellum (i.e. cerebellar cortex), ventral region of the forebrain (e.g., striatum, caudate, putamen, globus pallidus, nucleus accumbens; septal nuclei, subthalamic nucleus); regions and nuclei of the thalamus and hypothalamus; regions and nuclei of the deep cerebellum (e.g., dentate nucleus, globose nucleus, emboliform nucleus, fastigial nucleus) and brainstem (e.g., substantia nigra, red nucleus, pons, olivary nuclei, cranial nerve nuclei); and regions of the spine (e.g., anterior horn, lateral horn, posterior horn)) may be prepared post-mortem by the subject methods and the connectivity of the neurons therein microscopically analyzed, e.g. obtained, stored, rendered, used, and actuated, e.g., to provide the full connectivity of a brain, e.g., a human brain, after death. Such studies will contribute greatly to the understanding of how the brain develops and functions in health and during disease, and of the underpinnings of cognition and personality.

As another example, the subject methods may be employed to evaluate, diagnose or monitor a disease. "Diagnosis" as used herein generally includes a prediction of a subject's susceptibility to a disease or disorder, determination as to whether a subject is presently affected by a disease or disorder, prognosis of a subject affected by a disease or disorder (e.g., identification of cancerous states, stages of cancer, likelihood that a patient will die from the cancer), prediction of a subject's responsiveness to treatment for a disease or disorder (e.g., a positive response, a negative response, no response at all to, e.g., allogeneic hematopoietic stem cell transplantation, chemotherapy, radiation therapy, antibody therapy, small molecule compound therapy) and use of therametrics (e.g., monitoring a subject's condition to provide information as to the effect or efficacy of therapy). For example, a biopsy may be prepared from a cancerous tissue and microscopically analyzed to determine the type of cancer, the extent to which the cancer has developed, whether the cancer will be responsive to therapeutic intervention, etc.

As another example, a biopsy may be prepared from a diseased tissue, e.g. kidney, pancreas, stomach, etc., to determine the condition of the tissue, the extent to which the disease has developed, the likelihood that a treatment will be successful, etc. The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease. The terms "individual," "subject," "host," and "patient," are used interchangeably herein and refer to any mammalian subject for whom diagnosis, treatment, or therapy is desired, particularly humans. Examples of diseases that are suitable to evaluation, analysis, diagnosis, prognosis, and/or treatment using the subject methods and systems include, but are not limited to, cancer, immune system disorders, neuropsychiatric disease, endocrine/reproductive disease, cardiovascular/pulmonary disease, musculoskeletal disease, gastrointestinal disease, and the like.

The subject methods may also be used to evaluate normal tissues, organs and cells, for example to evaluate the relationships between cells and tissues of a normal tissue specimen, e.g., a tissue specimen taken from a subject not known to suffer from a specific disease or condition. The subject methods may be used to investigate, e.g., relationships between cells and tissues during fetal development, such as, e.g., during development and maturation of the nervous system, as well as to investigate the relationships between cells and tissues after development has been completed, e.g., the relationships between cells and tissues of the nervous systems of a fully developed adult specimen.

The subject methods also provide a useful system for screening candidate therapeutic agents for their effect on a tissue or a disease. For example, a subject, e.g. a mouse, rat, dog, primate, human, etc. may be contacted with a candidate agent, an organ or a biopsy thereof may be prepared by the subject methods, and the prepared specimen microscopically analyzed for one or more cellular or tissue parameters. Parameters are quantifiable components of cells or tissues, particularly components that can be accurately measured, desirably in a high throughput system.

The subject methods may also be used to visualize the distribution of genetically encoded markers in whole tissue at subcellular resolution, for example, chromosomal abnormalities (inversions, duplications, translocations, etc.), loss of genetic heterozygosity, the presence of gene alleles indicative of a predisposition towards disease or good health, likelihood of responsiveness to therapy, ancestry, and the like. Such detection may be used in, for example, diagnosing and monitoring disease as, e.g., described above, in personalized medicine, and in studying paternity.

As used herein the phrase "diagnostic" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

As used herein the phrase "diagnosing" refers to classifying a disease or a symptom, determining a severity of the disease, monitoring disease progression, forecasting an outcome of a disease and/or prospects of recovery. The term "detecting" may also optionally encompass any of the above.

In some embodiments, the enlarged sample can be re-embedded in a non-swellable polymer. "Re-embedding" comprises permeating (such as, perfusing, infusing, soaking, adding or other intermixing) the sample with the non-swellable polymer, preferably by adding precursors thereof. Alternatively or additionally, embedding the sample in a non-swellable polymer comprises permeating one or more monomers or other precursors throughout the sample and polymerizing and/or crosslinking the monomers or precursors to form the non-swellable polymer or polymer. In this manner the first enlarged sample, for example, is embedded in the non-swellable polymer. Embedding the expanded sample in a non-swellable polymer prevents confrontational changes during sequencing despite salt concentration variation. The non-swellable polymer can be charge-neutral hydrogels. For example, it can be polyacrylamide hydrogel, composed of acrylamide monomers, bisacrylamide crosslinker, ammonium persulfate (APS) initiator and tetramethylethylenediamine (TEMED) accelerator.

In some embodiments, the fixed biological sample is subjected to passivation. As used herein the term "passivation" refers to the process for rendering the sample less reactive with the components contained within the fixative such as by functionalizing the fixative with chemical reagents to neutralize charges within. For example, the carboxylic groups of acrylate, which may be used in the swellable gel, can inhibit downstream enzymatic reactions. Treating the swellable gel composed of acrylate with 1-Ethyl-3-(3-dimethylaminopropyl)carbodiimide (EDC) and N-Hydroxysuccinimide (NHS) allows primary amines to covalently bind the carboxylic groups to form charge neutral amides and passivate the swellable gel.

The innovation enables physical expansion of common clinical tissue specimen based on the unique physical and chemical properties of clinical tissue specimens. Clinical tissue specimens are usually highly fixed, tightly attached on the superfrost glass slides, and embedded in the paraffin (or stained and mounted in a mounting medium) for long-term storage. Some clinical tissue specimens are stained with dyes, such as hematoxylin and eosin (H&E), which are incompatible with fluorescence imaging. To apply ExM to clinical samples, de-paraffinization, antigen retrieval and aggressive protease digestion are integrated in a comprehensive workflow to handle various kinds of common clinical specimens. De-paraffinization and antigen retrieval address the recovery of archived clinical samples, while aggressive protease digestion is critical for the success of sample expansion, as most of the human tissues contain abundant hard-to-digest structural proteins, such as collagen and fibronectin, which prevent homogeneous expansion of the sample. Taken together, the present invention allows for the application of ExM to the enormous amount of archived clinical samples and enable super-resolution optical interrogations of mechanisms of a broad range of diseases by conventional optical microscopy.

This invention provides a comprehensive workflow to facilitate expansion of common types of clinical samples for super-resolution molecular imaging. The methods described herein will result in optimal outcomes, such as proper immunostaining, sufficient digestion of tissue, high quality of polymer synthesis, and maintenance of proteins of interest during expansion.

The invention also describes the reutilization of classic H&E stained slides for further biomolecular interrogation in nanoscale level. In general, H&E stained slides are not considered suitable for further downstream processing due to the difficulty in removing the stain and mounting medium. Thus, the invention describes a unique and cost-effective approach to overcome this barrier and enable the extraction of more information from the used H&E slides. In one embodiment, the method of expanding H&E stained slides for further utilization combines xylene-ethanol-water sequential washing, protein anchoring and in situ polymer synthesis.

EXAMPLES

Stock Solution
  Blocking buffer: MAXblock™ Blocking Medium
  Staining buffer: MAXbind™ Staining Medium
  Washing buffer: MAXwash™ Washing Medium
  Monomer Solution:

| Component | Stock concentration* | Amount (mL) | Final concentration* |
|---|---|---|---|
| Sodium acrylate | 38 | 2.25 | 8.6 |
| Acrylamide | 50 | 0.5 | 2.5 |
| N,N'-Methylenebisacrylamide | 2 | 0.50 | 0.10 |
| Sodium chloride | 29.2 | 4 | 11.7 |
| PBS | 10x | 1 | 1x |
| Water | | 1.15 | |
| Total | | 9.4** | |

*All concentrations in g/100 mL except PBS
**9.4/10 mL (1.06x), with the remaining 6% volume brought up by initiator, accelerator and inhibitor.

PBS: 1×PBS with 0.5% Triton-X
Gelling Solution: Mix the following on ice in the following order:
1. Monomer solution
2. accelerator
3. inhibitor
4. initiator Add the initiator last to prevent premature gelation. The mixture can be vortexed to ensure full mixing.

Digestion Buffer
50 nM Tris
20% wt/vol SDS
25 mM EDTA
0.5% Triton-X
pH=8.0

100 mM beta-mercaptoethanol can be added prior to adding tissue and incubation. The mixture can be vortexed to ensure full mixing. The sample is incubated at 37° C. for 24 hrs and then 30 min steamed autoclaved cycle, followed by a 30 min cool down in autoclave and then wash×3 in PBST Multiplexed ExPath Protocol for Fixed Human Tissues Sample Pre-Processing Formalin fixed paraffin embedded (FFPE) clinical samples of 5-10 um thick of human normal brain and brain tumor samples. In addition, 5 um thick FFPE tissue microarrays (TMA) from US Biomax of human normal brain and glioma brain tumors were used.

For H&E stained slides, hematoxylin and eosin are eliminated during the expansion process.

For unfixed frozen tissue slides in optimum cutting temperature (OCT) solution (Tissue-Tek), fix the tissues for 10 min in cold acetone at −20° C. before washing with 1×PBS solution 3 times for 10 min at RT.

FFPE clinical samples were rehydrated by sequential placement in solutions of xylene ×2, 100% EtOH, 95% EtOH, 80% EtOH, 50% EtOH and doubly deionized water at room temperature (RT) 3 min each.

For already fixed, frozen clinical tissue sections, leave slides at RT for 2 mins to let the OCT, melt and then wash 3× with PBS solution at RT for 5 min each.

Stain with 2 ug/ml of DAPI in 1×PBS for 30 min at RT, cover tissue section with 1×PBS and take pre-expansion images on a microscope, so that expansion factor and thus biological units of length can be established later.

Anchoring Treatment

All tissues used here, whether they had undergone prior immunohistochemistry for isotropy validation and epitope unmasking analysis, or unstained tissues for tissue multiplexing, were treated with the anchoring, gelation, and digestion steps noted here. Acryloyl-X (6-((acryloyl)amino) hexanoic acid, succinimidyl ester, here abbreviated AcX, Thermo Fisher Scientific) powder was dissolved in anhydrous DMSO at a concentration of 10 mg/ml and stored in aliquots in a desiccated environment at −20° C. Tissue proteins were chemically modified with an acrylamide group to enable subsequent anchoring into the hydrogel polymer by incubation with AcX at a concentration of 0.1 mg/ml in 1×PBS with 0.5% Triton-X for 1.5 hrs at RT and 1.5 hrs at 37 C and then washed with 1×PBS three times for 5 min each.

Gelling

Monomer solution composed of 1×PBS, 2 M NaCl, 8.625% (w/w) sodium acrylate, 2.5% (w/w) acrylamide and 0.10% (w/w) N,N'-methylenebisacrylamide (Sigma-Aldrich) was prepared, aliquotted and stored at −20° C. Gelling solution was composed of monomer solution and the chemicals 4-hydroxy-2,2,6,6-tetramethylpiperidin-1-oxyl (4HT, Sigma-Aldrich) as an inhibitor, tetramethylethylenediamine (TEMED, Sigma-Aldrich) as an accelerator and ammonium persulfate (APS, Sigma-Aldrich) as an initiator. These components were added sequentially to the monomer solution to prepare the gelling solution with APS added last (final concentration, 0.01% (w/w) for 4HT and 0.2% (w/w) for both APS and TEMED). Tissue slides were covered with gelling solution and a gel chamber constructed by putting a coverslip on top of the tissue with spacers on either end of the tissue to avoid compression, ensuring the tissue was covered with gelling solution. Samples were first incubated at 4° C. for 1.5 hrs in a humidified atmosphere to prevent premature gelation and enable diffusion of solution into tissues, and subsequently incubated at 37° C. for 1.5 hrs in a humidified atmosphere to complete gelation.

Digestion

Tissues were incubated in homogenization buffer (20% SDS, 0.5% Triton-X, 25 mM EDTA, 100 mM β-mercaptoethanol, pH 8) for 30 min at 37 C and 1 hr in an autoclave at 120° C. Tissues detached from slides during digestion or immediately after following gentle shaking and washed with 1×PBS 5 times for 3 min each at RT. Gelled tissues not undergoing further immunostaining were incubated only in 2 ug/ml DAPI solution in 1×PBS for at least 30 min and washed three times with 1×PBS for 3 min each. Gels were then placed in doubly deionized water at RT for 5 min to enable expansion and repeated three to five times with fresh water until size of the expanded sample stabilized.

Primary Antibody Staining.

Samples were blocked with MAXblock Blocking Medium (Active Motif) for 1 hr at 37° C. followed by incubation with primary antibodies dissolved in MAXbind Staining Medium (Active Motif) at typical dilution of 1:100 for 12 hrs at 4° C. or 2 hrs at 37° C. and then washed in MAXwash Washing Medium (Active Motif) ×2 for 5 min each at RT.

Secondary Antibody Staining

Samples can be incubated with secondary antibodies dissolved in MAX staining buffer for 1.5-3 hrs at 37° C. or overnight at 4° C. and then washed in MAXwash buffer.

The samples can be further washed with PBST buffer at RT and stain with 2 ug/mL of DAPI in PBST for 15-30 mins at RT, then washed with PBST for ~5 min at RT.

All the primary and secondary antibodies and concentrations used in this work are commercially available and used at concentrations from 1:20 to 1:1000. Secondary antibodies were all used at a dilution of 1:500 (4 ug/ml).

Expansion

For expansion, remove the PBS and wash the samples with excess volume of ddH$_2$O, 3-5 times, for 10 minutes each time at RT. Slice expansion should reach a plateau after about the 3$^{rd}$ or 4$^{th}$ wash.

Imaging

Image with conventional fluorescent, confocal microscope, or other desired scopes.

Isotropy Validation

Tissue Processing. A normal brain and glioblastoma TMA (US Biomax) of 5 um thickness was prepared using the rehydration, antigen retrieval, and pre-expansion immunostaining steps delineated above. The normal brain TMA was stained with three primary antibodies: chicken anti-MAP2 and mouse anti-GFAP. The glioblastoma TMA was stained with three primary antibodies: chicken anti-vimentin and mouse anti-GFAP. Both TMAs were then incubated in the same secondary antibodies (goat anti-chicken Alexa Fluor 488 and goat anti-mouse Atto647N) followed by DAPI and mounted in VectaShield mounting media (Thermo Fisher).

Gels were incubated in 2 ug/ml DAPI solution in 1×PBS for at least 30 min and washed three times with 1×PBS for 3 min each.

Imaging. A Deltavision OMX Blaze (GE Healthcare) SR-SIM microscope with a 100×1.40 NA (Olympus) oil objective was used for super-resolution structured illumination microscopy (SR-SIM) of pre-expansion tissues. Tissues where washed in 1×PBS×5 for 5 min each to remove coverslip and mounting media. Tissues then underwent anchoring, gelation, digestion, and expansion steps as noted above. All post-expansion images were acquired on an Andor spinning disk (CSU X1 Yokogawa) confocal system coupled to a Nikon Ti-E microscope with a 40×1.15 NA water immersion objective. Combinations were as follows for excitation lasers and emission filters: DAPI, 405 nm excitation laser, 450/50 emission filter; Alexa Fluor 488, 488 excitation laser, 525/40 emission filter; Alexa Fluor 546 and CF543, 561 excitation laser, 607/36 emission filter; Atto 647N and CF 640R, 640 excitation laser, 685/40 emission filter. Expanded gels were placed in glass bottom six-well plates with all excess liquid removed. All images here are MIPs of equivalent size accounting for pre-expansion and post-expansion units.

Measurement error quantification. A distortion vector filed calculation and root mean square (RMS) error calculation was performed on corresponding z planes of pre-expansion and post-expansion images using Matlab (Mathworks). RMS error (um) was plotted as a function of measurement length (um).

Epitope De-Crowding and Unmasking Quantification

Tissue Re-staining. Normal brain and glioblastoma samples were re-stained following the same immunostaining protocol and conditions with primary and secondary antibodies. Gels were incubated in 2 ug/ml DAPI solution in 1×PBS for at least 30 min and washed three times with 1×PBS for 3 min each. Gels were then placed in doubly deionized water at RT for 5 min to enable expansion and repeated three to five times with fresh water until size of the expanded sample stabilized.

Imaging. All pre- and post-expansion images were acquired on a spinning disk confocal microscope with a 40×1.15 NA water immersion objective as described in "Isotropy Validation".

Epitope Unmasking Quotient Quantification. Pre-expansion z planes with post-expansion z-planes were matched using a feature based automated registration approach. Briefly, the VLFeat open source library was used to generate scale invariant feature transform (SIFT) key points using the same channel for registration for all possible combinations of pre-expansion z-planes and post-expansion z-projections (one pre-expansion z-plane would correspond to one post-expansion z-projection made up of 4-5 post-expansion z-planes) and a random sample consensus (RANSAC) algorithm was then use to filter out mismatches. The pair of pre-expansion z-plane and post-expansion z-projection with the largest number of SIFT key points was used for image registration (rotation, translation, scaling). For each sample (n=3 for each epitope evaluated) a region of interest (ROI) analysis was performed to quantify an unmasking quotient. Briefly, for each epitope evaluated (e.g., MAP2), an ROI of positive MAP2 staining corresponding to a known structure (e.g., neuron, axon) on the pre-expansion image was divided by an ROI of negative MAP2 (e.g., nucleus, GFAP positive only). Since the final processed pre-expansion and post-expansion images occupy the same space, then each coordinate in the pre-expansion image matches the post-expansion image. For each sample 5 ROTs were evaluated with the mean (s.e.m.) calculated, for both pre-expansion and the corresponding post-expansion image ROTs.

Antibody Removal Validation

Tissue Staining. Glioblastoma TMAs (n=4) were processed for ExM (rehydration, anchoring, gelation, homogenization, expansion), and immunostained with three primary antibodies: chicken anti-vimentin, rabbit anti-Tomm20, and mouse anti-GFAP for 2 hrs at 37° C. They were then washed with MAXWash buffer (Active Motif) three times for 3 min each, incubated in secondary antibodies (donkey anti-rabbit Alexa Fluor 488, donkey anti-chicken CF543, and donkey anti-mouse CF640R) for 2 hrs at 37° C., washed three times for 3 min each and then incubated, in 2 ug/ml DAPI solution in 1×PBS for at least 30 mini at RT and washed three times with 1×PBS for 3 min each.

Antibody Removal. For antibody removal, each TMA was incubated in digestion buffer at 70° C. and images acquired at four time points denoting incubation time in antibody removal buffer (t=0 min, t=45 min, t=90 min, t=135 min, and t=180 min).

Imaging. All images were acquired on a spinning disk confocal microscope with a 40×1.15 NA water immersion objective as described in "Isotropy Validation". For each glioblastoma TMA (n=4), the same three areas were imaged at each time point at the same settings.

Image Processing. All time points were registered to time point t=0. Time point t=0 z-planes were matched with all other time points t>0 using a similar approach as in "Epitope Unmasking Quantification". SIFT key points were generated using the DAPI channel for registration for a z-projection made up of 10 z-planes from baseline image (time point t=0) and all possible z-projections made up of 10 z-planes for each time point t>0 images, and a RANSAC algorithm was then used to filter out mismatches. The pair of baseline z-projection and each t>0 time point z-projection with the largest number of SIFT key points was used for image registration (rotation, translation, scaling). Once registered, for each area image (n=4 TMAs and 3 areas per TMA), five 50 um diameter region of interest (ROT) were selected. The ROIs were used to calculate mean fluorescence signal intensity for each fluorescence channel (Alexa Fluor 488, CF543, and CF 640R).

Results

Protein Denaturation and Conservation for Optimized Multiplexed Expansion Microscopy The most common clinically available tissue state in formalin fixed paraffin embedded (FFPE) normal and brain tumor tissue samples were used. Clinical samples are 5-10 um thick and adherent unto a glass slide. Tissue deparaffinization and rehydration (e.g., xylene, graded EtOH, water washes) was performed to prepare samples for protein denaturation and preservation multiplexed ExM protocol (here abbreviated multiExM).

Figures 2A, 2B, 2C, 2D, 2E, 2F:
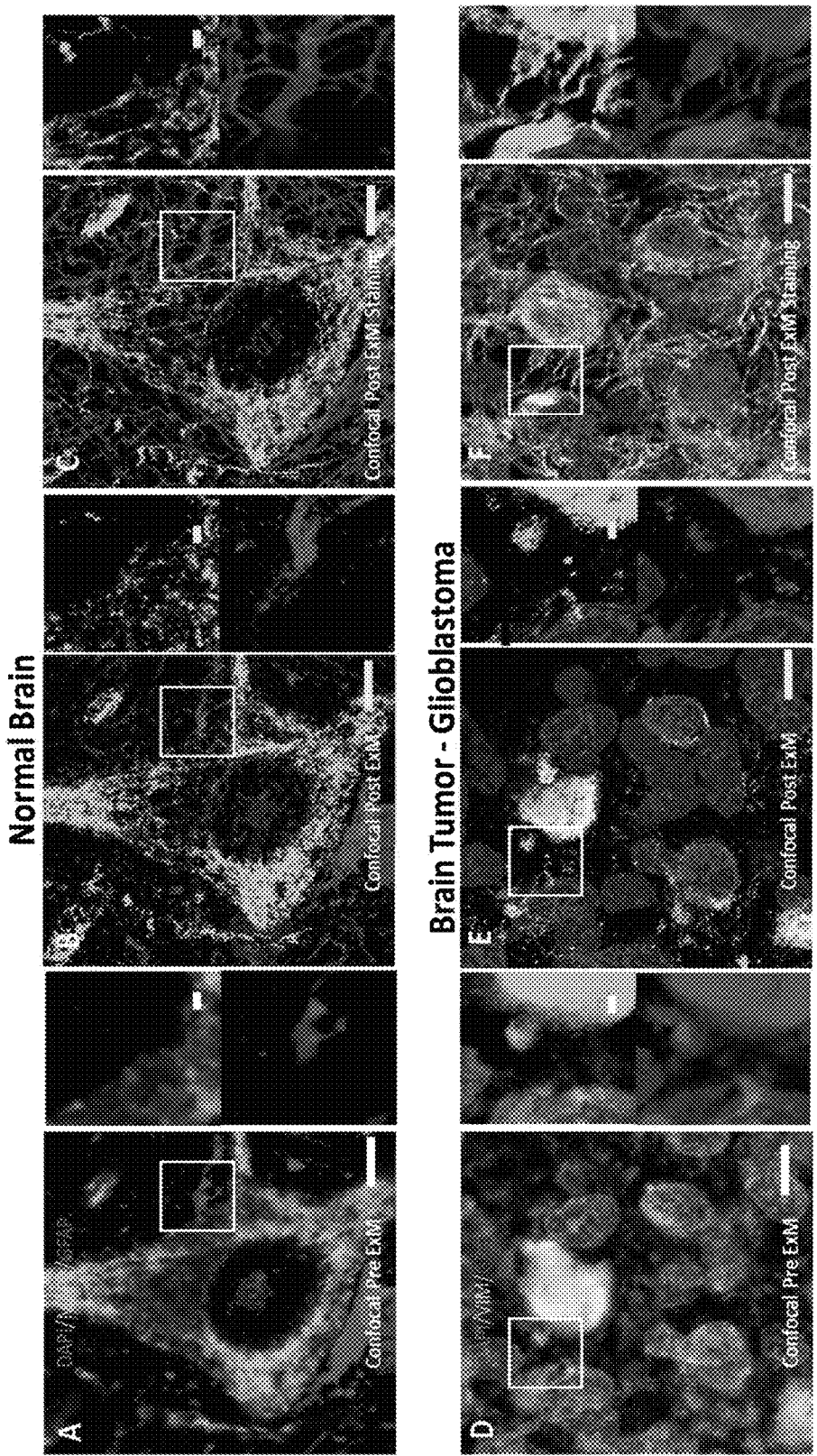
FIG. 2A through FIG. 2F Super-resolution Epitope Unmasking in Multiplexed ExM of Normal Brain and Brain Tumors. Pre-expansion images in FIG. 2A of a tissue microarray core of normal human hippocampus acquired with a spinning disc confocal microscope. Post-expansion images in FIG. 2B without post expansion staining and FIG. 2C with post-expansion staining acquired with a spinning disc confocal microscope of same area as FIG. 2A DAPI; MAP2; glial fibrillary acid protein. Pre-expansion images in FIG. 2E of a tissue microarray core of human glioblastoma acquired with a spinning disc confocal microscope. Post-expansion images in FIG. 2E without post expansion staining and FIG. 2F with post expansion staining acquired with a spinning disc confocal microscope of same area as FIG. 2D. Insets show magnified views of boxed regions in FIGS. 2A-F DAPI; vimentin; glial fibrillary acid protein. Scale bars.
Figure 3A:
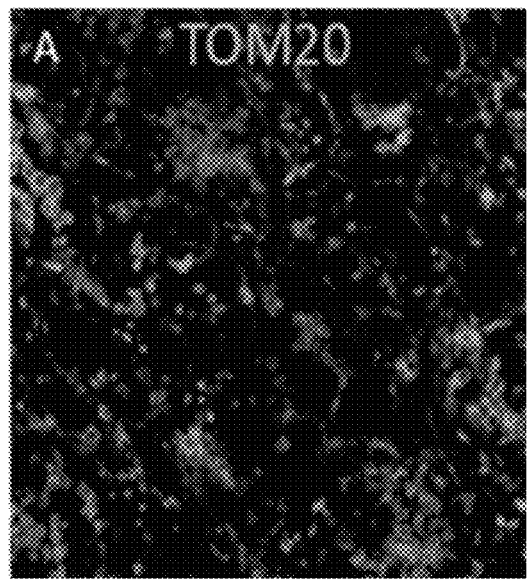
FIG. 3A through FIG. 3I Antibody Removal and Epitope Preservation for Multi-Round Staining in Multiplexed ExM. Post-expansion images of a tissue microarray core of glioblastoma acquired with a spinning disc confocal fluorescence microscope; mitochondria marker Tomm20 with AlexaFluor488 dye conjugated secondary antibody; vimentin with CF543 dye conjugated secondary antibody; glial acid fibrillary protein with CF640R dye conjugated secondary antibody.
Figure 3B:
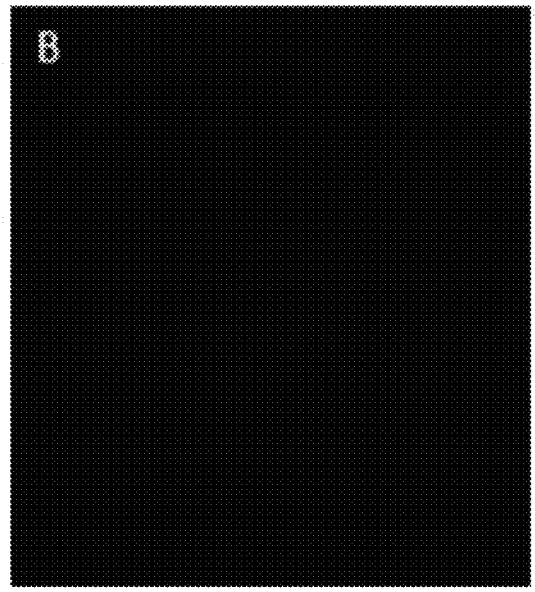
Figure 3C:
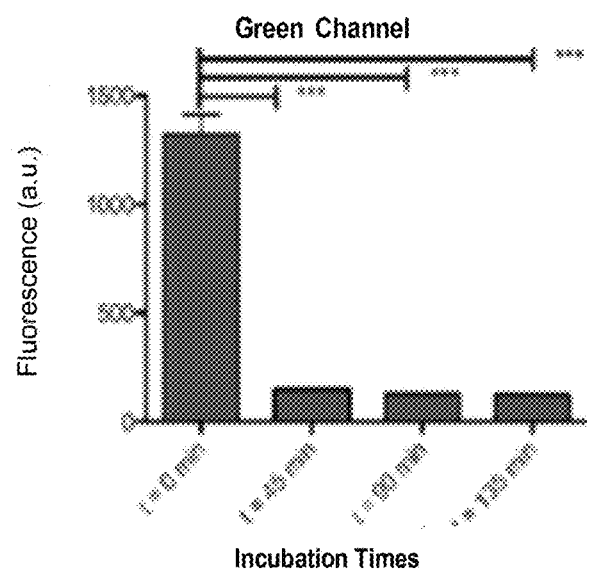
Figure 3D:
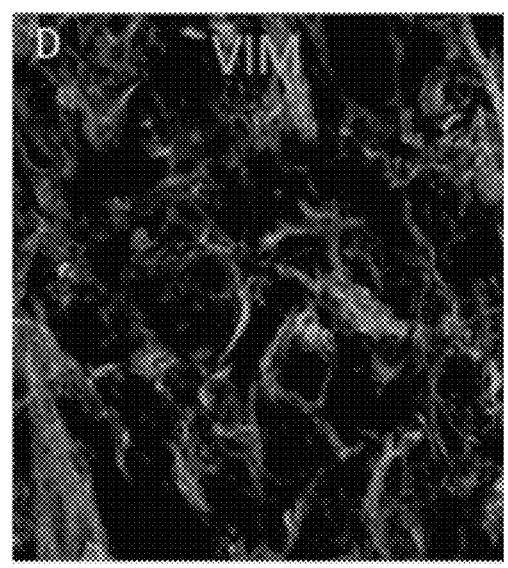
Figure 3E:
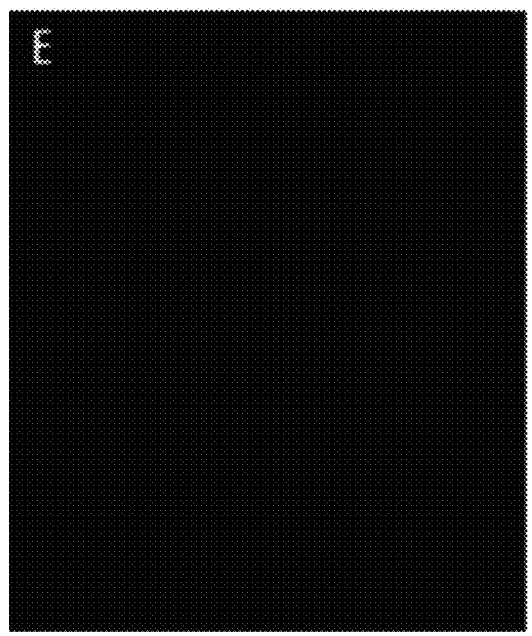
Figure 3F:
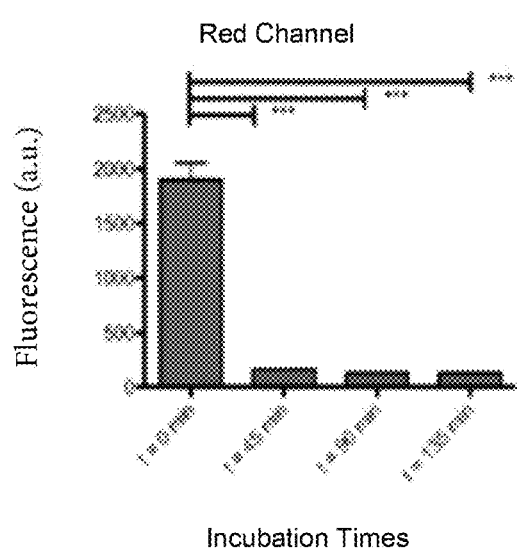
Figure 3G:
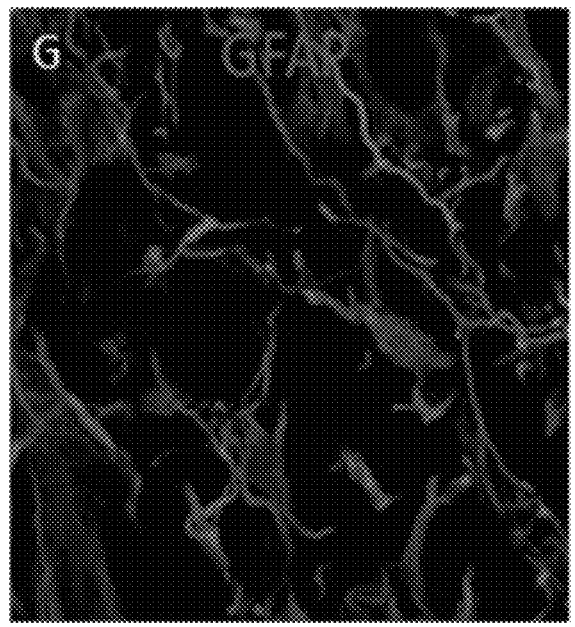
Figure 3H:
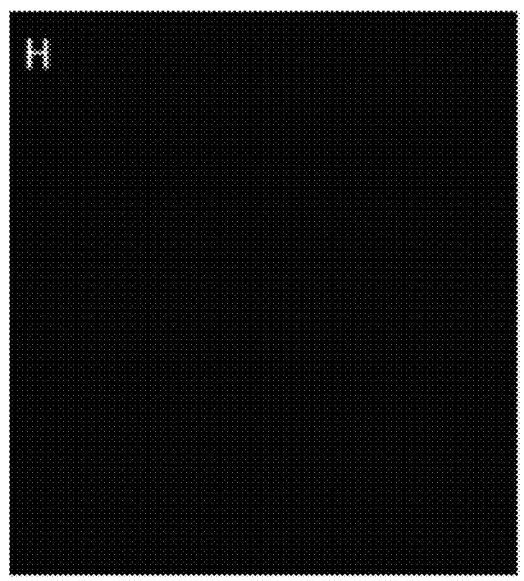
Figure 3I:
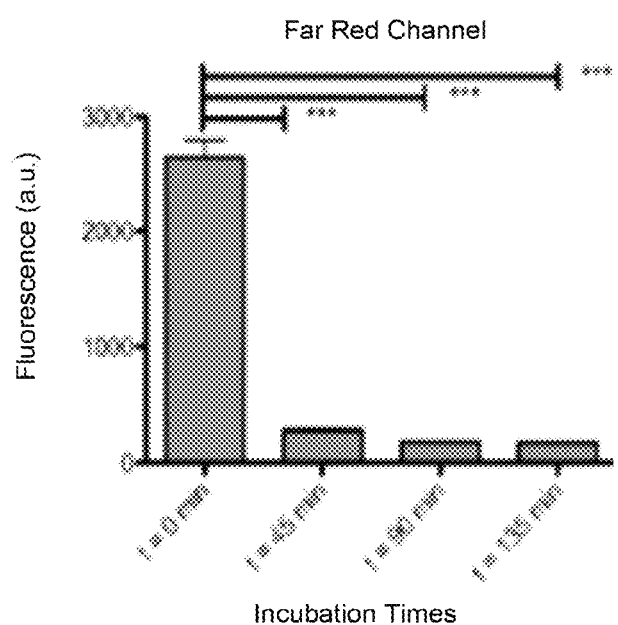

Gel-embedded tissues were treated with high temperatures in denaturing, non-enzymatic conditions to mechanically soften tissues and enable isotropic expansion and retention of epitopes for multiple rounds of immunostaining post-expansion. Gel embedded tissues (e.g., normal brain and brain tumor) treated at high temperatures (60 min autoclave) with a solution containing a high concentration of anionic detergent (20% sodium dodecyl sulfate (SDS) pH 8) in reducing conditions (100 mM β-mercaptoethanol), resulted in excellent isotropic expansion. The low distortion obtained by using this protocol on human clinical archival samples of both normal brain (FIG. 2a-c) and glioblastoma (FIG. 2d-f) tissues was validated using super-resolution structured illumination microscopy (SR-SIM) pre-expansion and diffraction limited confocal microscopy post-expansion. Tissues were treated with xylene to remove paraffin followed by rehydration and antigen retrieval (20% SDS, 0.5% Triton-X, 100 mM β-mercaptoethanol, pH 8 for 60 min at room temperature), prior to standard immunohistochemistry (block tissue followed by a primary antibody incubation and a secondary antibody incubation). Tissue anchoring, gelling and homogenization were performed in denaturing conditions. Imaging pre-expansion with confocal microscopy or SR-SIM followed by imaging post-expansion yielded low distortion levels in both normal human brain (FIGS. 2b and c) and human glioblastoma (FIGS. 2e and f). Furthermore, consistent expansion across tissues was obtained with an average expansion factor of ~4×. Thus, this protocol for multiplexed ExM yielded highly isotropic expansion of clinical samples in both normal and brain tumor tissues.

Post-expansion tissues unmasked epitopes across multiple different targets (e.g., vimentin, GFAP, MAP-2) in both normal human brain and human glioblastoma (FIG. 3). Tissues underwent rehydration, antigen retrieval, immunohistochemistry, anchoring, gelling and homogenization followed by a post-digestion immunostaining using the same immunostaining conditions. Post-expansion stained images demonstrated significant areas of enhanced immunostaining not previously visualized in the pre-expansion images, with unmasking quotient of up to 10-50% depending on epitope (e.g., GFAP, MAP2, vimentin, neurofilamen 70, β-III-tubulin). Unmasking quotient was defined as the net area of unmasked signal in the post-expansion restained images compared to the pre-expansion images (FIG. 3). Thus, the methods described herein can de-crowd and unmask previously inaccessible epitopes by both pulling epitopes apart creating space for antibodies to access as well as break protein cross-linkages to enable antibody staining, providing a likely explanation for enhanced immunostaining with this technique.

Figures 6A, 6B, 6C, 6D, 6E, 6F, 6G, 6H:
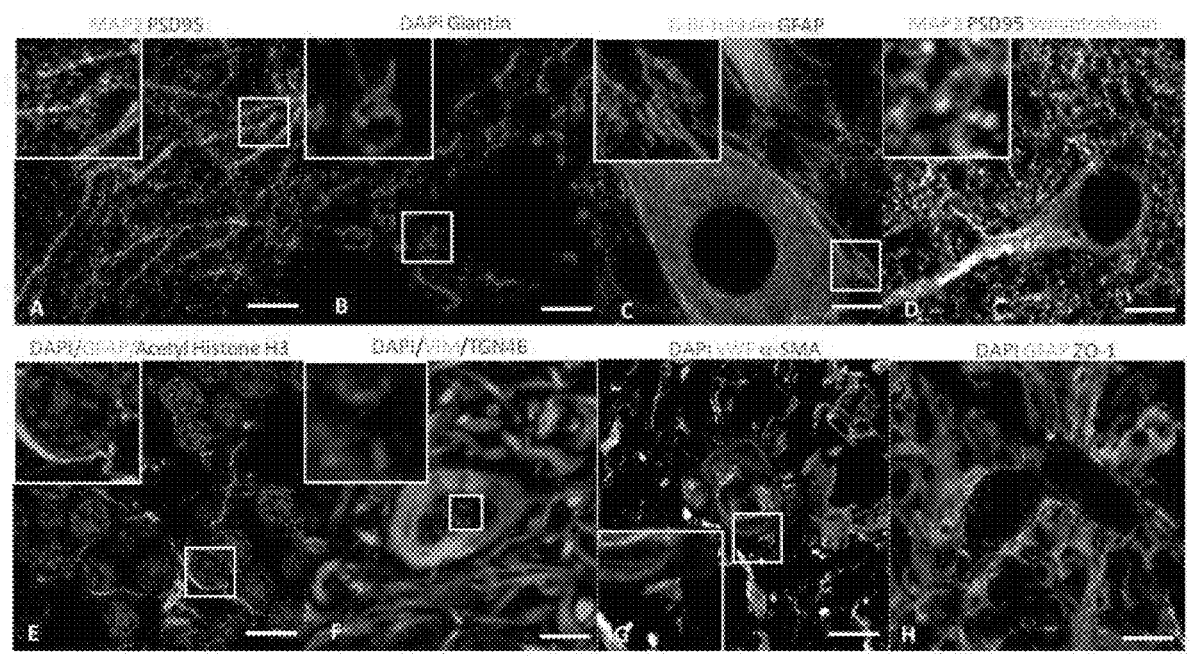
FIG. 6A through 6H demonstrates that post-expansion immunostaining was possible across a broad range of both normal and brain tumor tissues without the need for pre-expansion immunostaining.

The present invention provides a protein preservation and denaturation protocol that can preserve epitopes to enable post-expansion immunostaining with commercially available antibodies. Post-expansion immunostaining was possible across a broad range of both normal and brain tumor tissues without the need for pre-expansion immunostaining (FIG. 6). A broad range of commercially available antibodies for intracellular and extracellular targets were evaluated in both native, non-expanded tissue using standard immunohistochemistry as well as in post-expanded tissues (FIG. 6). To validate the immunostaining, comparable features and immunostaining patterns were determined in both native tissues and post-expanded tissues. ExM uncovered sub-diffraction limited sized features of glial fibrillary acidic protein found in tumors cells important in GBM tumor cell migration and progression of the tumor perivascular niche (FIG. 6). Thus, the multiExM protocol leads to proteome preservation, enabling probing of expanded tissues with commercially available antibodies across a broad range of targets and as well as with potential epitope de-crowding and unmasking of epitopes in both normal and glioblastoma human tissues (FIG. 3).

Figures 4A, 4O:
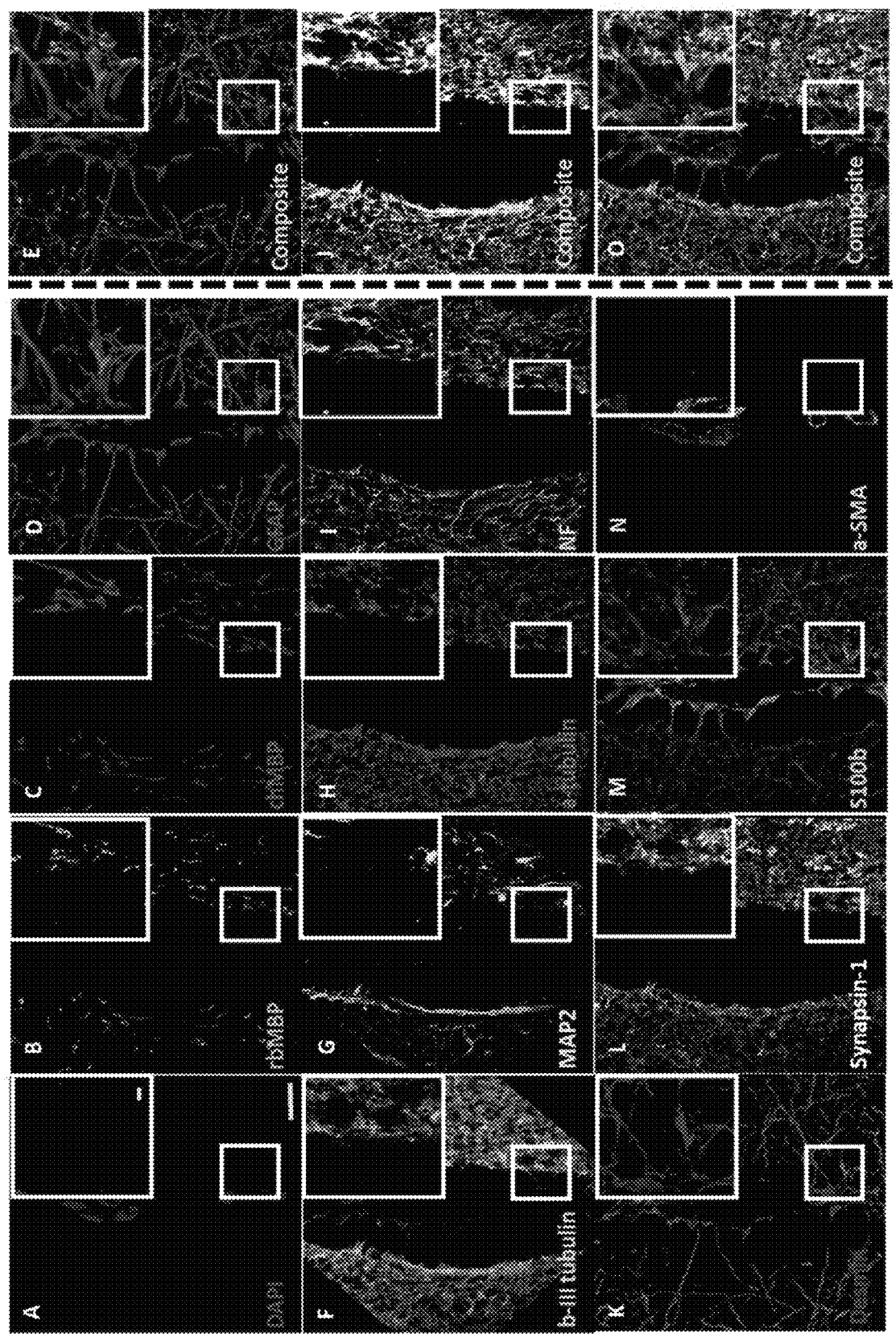
FIG. 4A through FIG. 4O Multiplexed ExM of Normal Human Hippocampus at gliovascular interface.

Post-expansion immunostained samples can undergo removal of antibodies at high temperatures and denaturing conditions to enable subsequent rounds of immunostaining. Clinical samples incubated at 70° C. in digestion buffer for at least 90 min resulted in destaining to background levels (FIG. 4 a-i). Further, samples were tested following a round of antibody removal with addition of secondary antibody only and found no significant change in signal, suggesting that the destaining process effectively eliminates the primary and secondary antibodies (FIG. 4 a-i). Next it was determined if epitopes undergo significant loss of antigenicity or distortion following multiple rounds of staining and destaining. No significant change in fluorescence signal or distortion following the staining and de-staining steps was found even after six rounds (FIG. 4) Thus, instant invention provides a robust means of treating gel embedded clinical samples that enables robust immunostaining with epitope preservation for quantitative multiplexing.

Figures 5A, 5B, 5C, 5D, 5E, 5F, 5G, 5H:
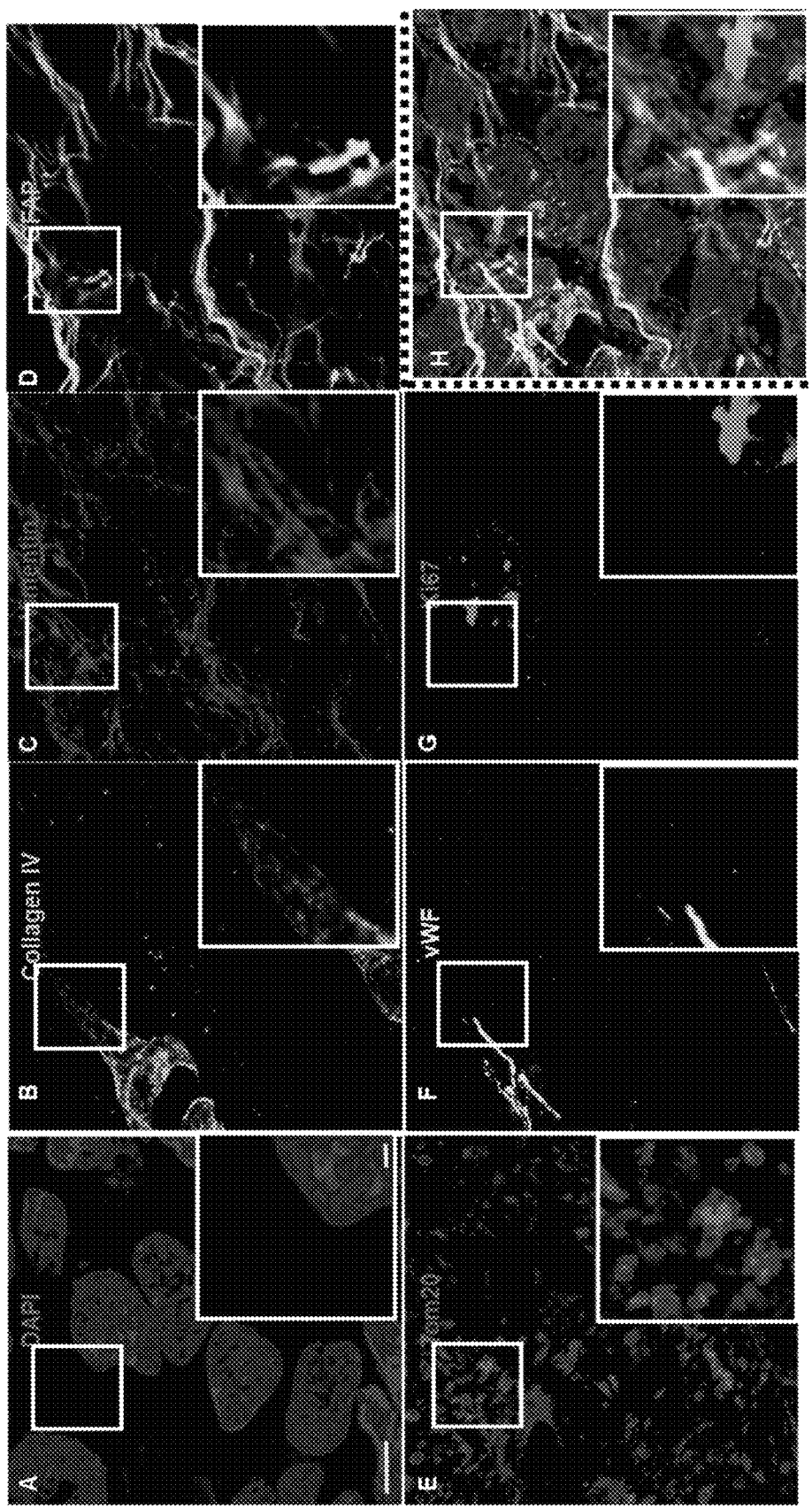
FIG. 5A through FIG. 5H Multiplexed ExM of Glioblastoma Perivascular Niche. Post-expansion images of the GBM tumor perivascular niche acquired with a spinning disc confocal microscope demonstrates at super-resolution scales clear association of migrating, proliferating tumor cells (Ki-67) along the tumor vasculature with enveloping astrocytic processes (GFAP, vimentin) distinct from vascular components (vWF,collagen).

The multiExM protocol (i.e., anchoring, gelling, homogenization, and multiple rounds of staining, destaining, restaining) was used to enable highly multiplexed imaging of both normal and glioma tissues. First multiExM was used to visualize the fine subcellular architecture of normal human hippocampus (FIG. 5). Antibodies to structural filaments specific to glial-neuronal cell types including microtubule associated protein-2, myelin basic protein, neurofilament, β-III-tubulin, GFAP, von Willebrand factor, and α-smooth muscle actin were used. Imaging of these structures at super-resolution length scales enabled clear differentiation of cell types and nanoscale-level structures without confounding and inaccurate co-localization encountered in pre-expansion, diffraction limited imaging (FIG. 5). Multiplexing of the neurovascular interface enabled super-resolution mapping of key structures to within vessels including collagen (COL4), endothelial cells (CD31 and vWF), and pericytes (α-SMA). Further, it also provided exquisite resolution of the fine astrocytic foot processes (GFAP) surrounding blood vessels, and the dense distinct network at the glial-vascular interface (FIG. 5).

Next, multiExM was used on glioblastoma samples. Here the complex network of components of the tumor perivascular niche were mapped, given its significant role in tumor growth and migration. First, main vascular and perivascular structures including collagen as a marker of the vascular basement membrane (COL4); vWF and CD31 as markers of endothelial cells; α-SMA as a marker of pericytes; endosialin as a specific marker of proliferating, angiogenic vessels; and VEGF as a cellular marker of cells undergoing active angiogenesis were mapped (FIG. 5). MultiExM enables highly multiplexed, super-resolution scale imaging to distinguish a diverse set of components of the tumor vasculature without confounding and inaccurate co-localization when imaged at diffraction limited scales. Staining with GFAP and vimentin enables visualization of individual cellular and tumor processes both in the peri-vascular region as well as specific astrocytic processes in direct contact with vessels (FIG. 5). Further, use of a cell cycle marker (Ki-67), a marker for non-mutated (i.e., normal, non-tumor) cells, and caspase-3, enabled further stratification of the cellular population around tie perivascular niche, including those undergoing active proliferation (Ki-67 positive), non-tumor cells (ATRX positive) and apoptotic cells (caspase-3 positive). The nanoscale capabilities of multiExM enabled resolution of nanoscopic features between the distinct cell types and the perivascular niche structures, including association between proliferating cell foot processes at the glial-vascular interface.

While this invention has been particularly shown and described with references to preferred embodiments thereof, it will be understood by those skilled in the art that various changes in form and details may be made therein without departing from the scope of the invention encompassed by the appended claims.

What is claimed:

1. A method for preparing an expandable biological specimen comprising the steps of
   (a) contacting the specimen with macromolecules that will bind to biomolecules within the specimen;
   (b) treating the specimen with a bifunctional crosslinker;
   (c) permeating the specimen with precursors of a swellable polymer;
   (d) polymerizing the precursors to form a swellable polymer within the specimen;
   (e) anchoring the biomolecules to the swellable polymer; and
   (f) incubating the specimen with about 20% w/v of a detergent in a buffer having a pH between about 4 and about 12, the buffer comprising about 5 mM to about 100 mM of a metal ion chelator; about 0.1% to about 1.0% of a nonionic surfactant; and 10-100 mM of an antioxidant.

2. The method of claim 1, wherein the expandable specimen is expanded by contacting the swellable polymer with a solvent or liquid to cause the swellable polymer to swell.

3. The method of claim 1, further comprising the step of incubating the specimen in antibodies to perform immunostaining following treatment with buffer.

4. The method of claim 3, further comprising treating the antibody-stained specimen with detergent buffer at 70° C. for 2-4 hrs to remove antibodies for sequential multiple rounds of immunostaining for antibody multiplexing.

5. The method of claim 1, wherein the specimen is a previously preserved clinical sample.

6. The method of claim 5, wherein the specimen is a formalin fixed paraffin embedded (FFPE) or a hematoxylin and eosin (H&E) stained tissue sample, or a fresh frozen sample, and wherein, prior to contacting step (a), the method further comprises the steps of
   (i) de-coversliping the specimen if it is mounted;
   (ii) subjecting the specimen to mounting medium removal if it is mounted; and
   (iii) subjecting the specimen to re-hydration if step (ii) is performed.

7. The method of claim 6, further comprising subjecting the specimen to antigen retrieval.

8. The method of claim 1, wherein the detergent is selected from sodium dodecyl sulfate (SDS).

9. The method of claim 1, wherein the buffer is selected from Tris, citrate, phosphate, bicarbonate, 3-morpholinopropane-1-sulfonic acid (MOPS), borate, [tris(hydroxymethyl)methylamino]propanesulfonic acid (TAPS), bicine, Tricine, (4-(2-hydroxyethyl)-1-piperazineethanesulfonic acid) (HEPES), 2-[(2-Hydroxy-1,1-bis(hydroxymethyl)ethyl)amino]ethanesulfonic acid (TES), and 2-(N-morpholino)ethanesulfonic acid (MES).

10. The method of claim 1, wherein the chelator is selected from ethylenediaminetetraacetic acid (EDTA), egtazic acid (EGTA), ethylenediamine-N,N'-bis (EDDHA), ethylenediamine-N,N'-disuccinic acid (EDDS), BAPTA, and DOTA.

11. The method of claim 1, wherein the surfactant is selected from polyethylene glycol tert-octylphenyl ether, octylphenol decaethylene glycol ether, polyethylene glycol sorbitan monolaurate, polyoxyethylene(20)sorbitan monooleate, sorbitan, polysorbate 20, polysorbate 80, polyethylene glycol (PEG), decyl glucoside, decyl polyglucose and cocamide diethanolamine (DEA).

12. The method of claim 1, wherein the antioxidant is selected from β-mercaptoethanol and dithiothreitol (DTT).

13. The method of claim 1, wherein the specimen is incubated in a buffer comprising 20% wt/vol SDS, 50 mM Tris, 25 mM EDTA, 0.5% octylphenol decaethylene glycol ether, and 100 mM β-mercaptoethanol.

14. The method according to claim 1, wherein the bifunctional crosslinker is succinimidyl ester of 6-((acryloyl)amino)hexanoic acid (AcX).

15. The method of claim 1, wherein prior to the contacting step (a) the sample is subjected to antigen retrieval.

16. The method of claim 15, wherein when the specimen is subjected to antigen retrieval the specimen is heated in a 20 mM sodium citrate solution at about 100° C.

17. A method of preparing an expandable biological specimen comprising the steps of
   (a) treating the specimen with a bifunctional crosslinker;
   (b) permeating the specimen with precursors of a swellable polymer;
   (c) polymerizing the precursors to form a swellable polymer within the specimen; and
   (d) incubating the specimen with about 20% w/v of a detergent in a buffer having a pH between about 4 and about 12, the buffer comprising about 5 mM to about 100 mM of a metal ion chelator; about 0.1% to about 1.0% of a nonionic surfactant; and 10-100 mM of an antioxidant.

18. The method of claim 17, wherein the expandable specimen is expanded by contacting the swellable polymer with a solvent or liquid to cause the swellable polymer to swell.

19. The method of claim 17, wherein the specimen is incubated in a buffer comprising 20% w/v SDS, 50 mM Tris, 25 mM EDTA, 0.5% octylphenol decaethylene glycol ether, and 100 mM β-mercaptoethanol.

20. The method of claim 17, wherein prior to the treating step (a) the specimen is subjected antigen retrieval.

21. The method according to claim 17, wherein the bifunctional crosslinker is succinimidyl ester of 6-((acryloyl)amino)hexanoic acid (AcX).

22. A method for expanding a swellable material-embedded biological specimen comprising:
   (a) incubating the specimen with about 20% w/v of a detergent in a buffer having a pH between about 4 and about 12, the buffer comprising about 5 mM to about 100 mM of a metal ion chelator; about 0.1% to about 1.0% of a nonionic surfactant; and 10-100 mM of an antioxidant; and
   (b) contacting the swellable polymer with a solvent or liquid to cause the swellable polymer to swell.

23. The method of claim 22, wherein the specimen is incubated in a buffer comprising 20% w/v SDS, 50 mM Tris, 25 mM EDTA, 0.5% octylphenol decaethylene glycol ether, and 100 mM β-mercaptoethanol.

* * * * *

UNITED STATES PATENT AND TRADEMARK OFFICE
CERTIFICATE OF CORRECTION

| | |
|---|---|
| PATENT NO. | : 11,802,822 B2 |
| APPLICATION NO. | : 17/111135 |
| DATED | : October 31, 2023 |
| INVENTOR(S) | : Quevedo et al. |

It is certified that error appears in the above-identified patent and that said Letters Patent is hereby corrected as shown below:

In the Specification

In Column 1, after Line 7 insert heading & paragraph:
--GOVERNMENT SUPPORT
This invention was made with government support under NS087724, R01 MH110932, and R01 NS102727 awarded by the National Institutes of Health. The government has certain rights in the invention.--

Signed and Sealed this
Eleventh Day of November, 2025

John A. Squires
*Director of the United States Patent and Trademark Office*